US011701663B2

(12) United States Patent
Motadel

(10) Patent No.: US 11,701,663 B2
(45) Date of Patent: Jul. 18, 2023

(54) PIPETTE TIP SYSTEM

(71) Applicant: Xcaliber Sciences, Inc., San Diego, CA (US)

(72) Inventor: Arta Motadel, San Diego, CA (US)

(73) Assignee: XCALIBER SCIENCES, INC., San Diego, CA (US)

( * ) Notice: Subject to any disclaimer, the term of this patent is extended or adjusted under 35 U.S.C. 154(b) by 0 days.

(21) Appl. No.: 17/487,394

(22) Filed: Sep. 28, 2021

(65) Prior Publication Data

US 2022/0410164 A1 Dec. 29, 2022

Related U.S. Application Data

(60) Provisional application No. 63/231,945, filed on Aug. 11, 2021, provisional application No. 63/228,081, filed on Jul. 31, 2021, provisional application No. 63/215,728, filed on Jun. 28, 2021.

(51) Int. Cl.
*B01L 9/00* (2006.01)
*B01L 3/02* (2006.01)

(52) U.S. Cl.
CPC ............. *B01L 9/543* (2013.01); *B01L 3/0275* (2013.01); *B01L 3/0279* (2013.01); *B01L 3/0286* (2013.01); *B01L 2200/025* (2013.01); *B01L 2200/026* (2013.01); *B01L 2200/0689* (2013.01); *B01L 2200/14* (2013.01); *B01L 2200/141* (2013.01); *B01L 2300/041* (2013.01); *B01L 2300/042* (2013.01); *B01L 2300/0816* (2013.01); *B01L 2300/123* (2013.01)

(58) Field of Classification Search
None
See application file for complete search history.

(56) References Cited

U.S. PATENT DOCUMENTS

| 6,098,802 A * | 8/2000 | Asa ........................ B01L 9/543 |
| | | 206/443 |
| 6,098,819 A | 8/2000 | Link |
| 2001/0012492 A1 * | 8/2001 | Acosta .................... B01L 9/543 |
| | | 422/65 |

(Continued)

FOREIGN PATENT DOCUMENTS

DE 19525258 A1 * 1/1997 ........... B65D 25/108

OTHER PUBLICATIONS

Written Opinion of the International Searching Authority dated Sep. 23, 2022 for PCT/US2022/032667 (9 pages).

*Primary Examiner* — Matthew D Krcha
(74) *Attorney, Agent, or Firm* — Manuel de la Cerra

(57) ABSTRACT

A pipette tip system for use with a plurality of pipette tips is disclosed that includes a support card and a support card lid. The support card includes an array of pipette tip receiver openings arranged in a N×M array, wherein the N is less than M. The support card further has a short-side card rail edge on an edge of the support card along the N side of the array, and a long-side card rail edge on an edge of the support card along the M side of the array. The support card lid includes a long-side lid rail edge extending from a support card first surface, which is adapted to slidably mate with the long-side card rail edge, and a short-side lid rail edge extending from a support card second surface, which is adapted to slidably mate with the short-side card rail edge.

11 Claims, 28 Drawing Sheets

(56) References Cited

U.S. PATENT DOCUMENTS

| | | | |
|---|---|---|---|
| 2008/0240999 A1* | 10/2008 | Timpson | B01L 9/543 422/400 |
| 2009/0065458 A1* | 3/2009 | Murray | B01L 9/543 211/85.18 |
| 2011/0236278 A1* | 9/2011 | Motadel | B01L 9/543 422/560 |
| 2019/0344258 A1 | 11/2019 | Motadel et al. | |
| 2020/0122136 A1 | 4/2020 | Blaszcak et al. | |

* cited by examiner 10 ul Extra Large 300 ul

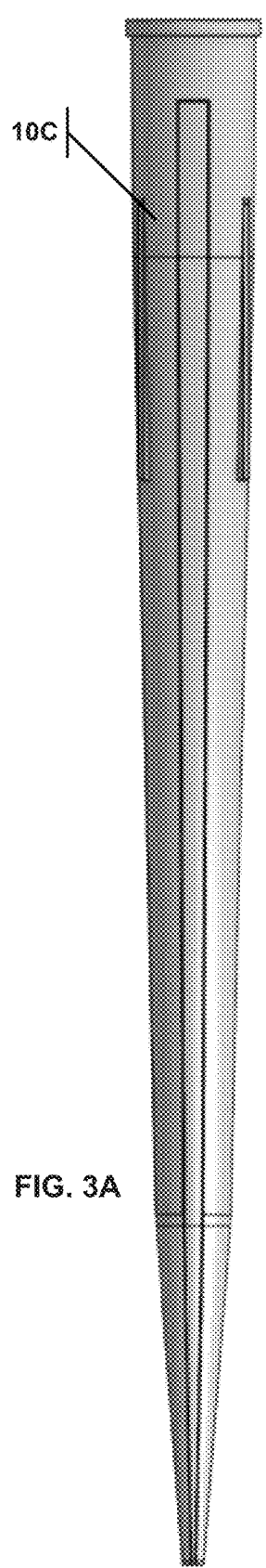
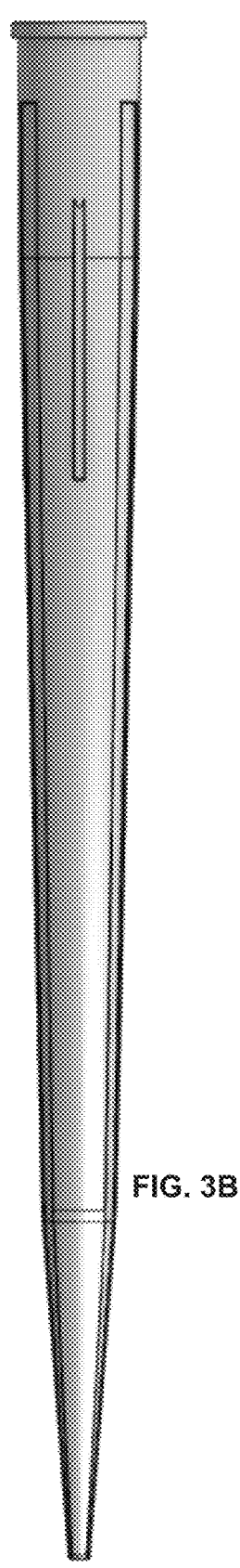
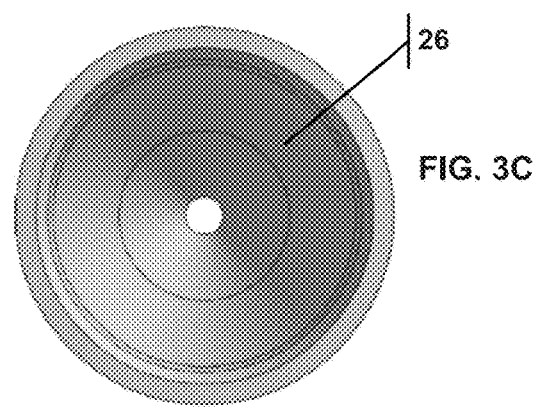
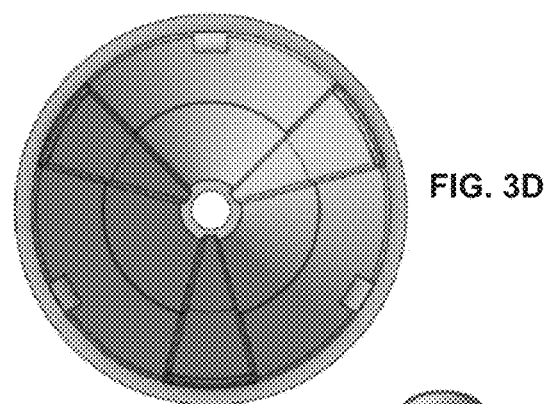
FIG. 3A
FIG. 3B
FIG. 3C
FIG. 3D
FIG. 3E
1200 ul

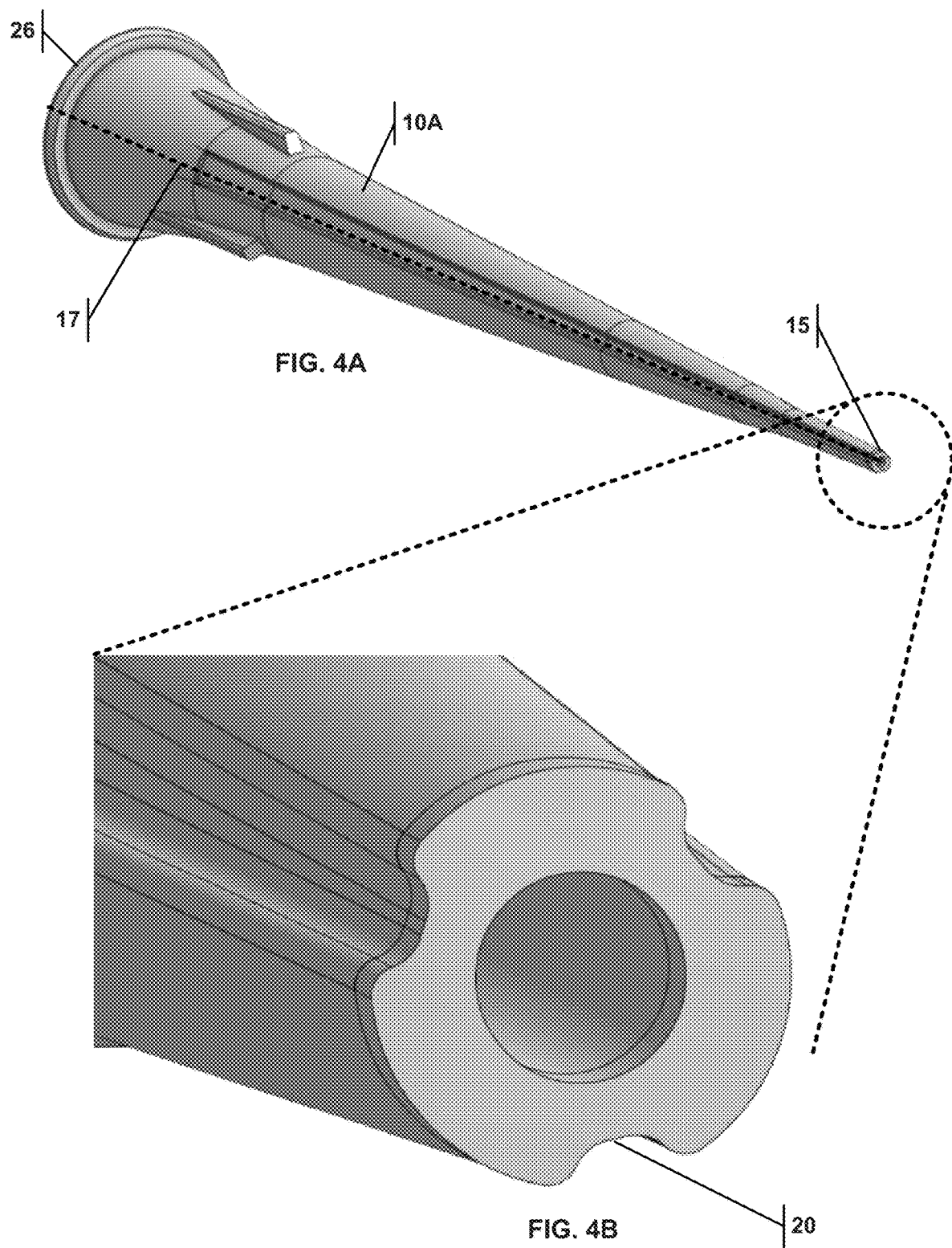

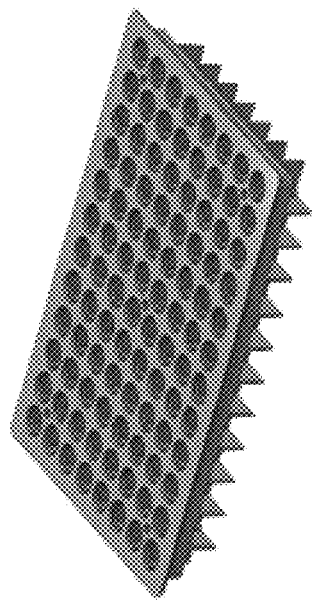
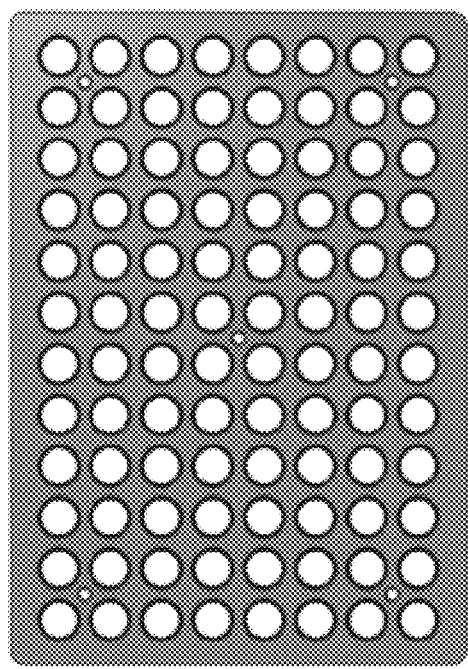
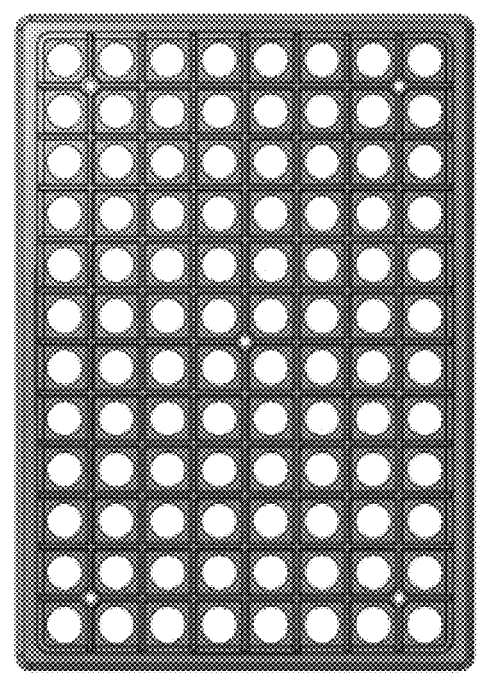
FIG. 7A  FIG. 7B  FIG. 7C  FIG. 7D  FIG. 7E

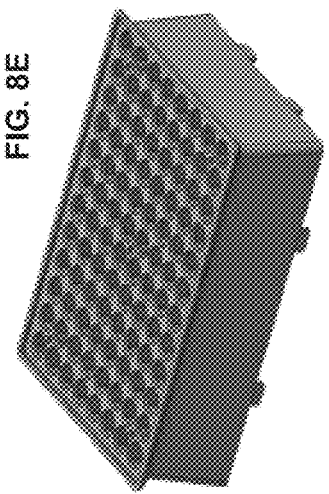
FIG. 8E
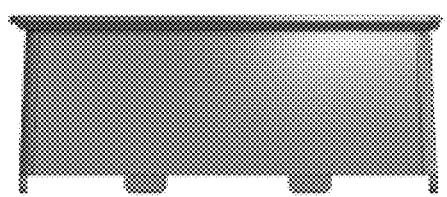
FIG. 8D
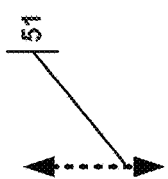
51
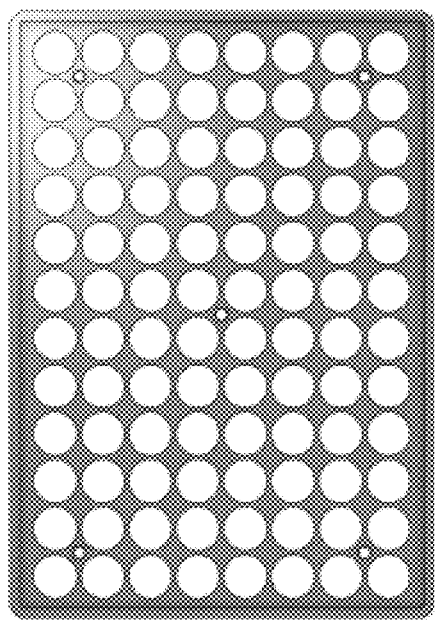
50B
FIG. 8A
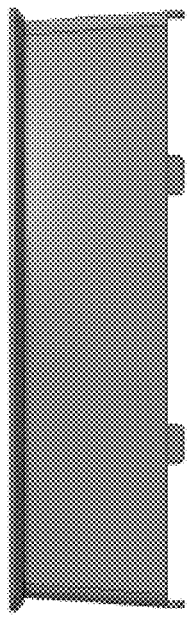
FIG. 8B
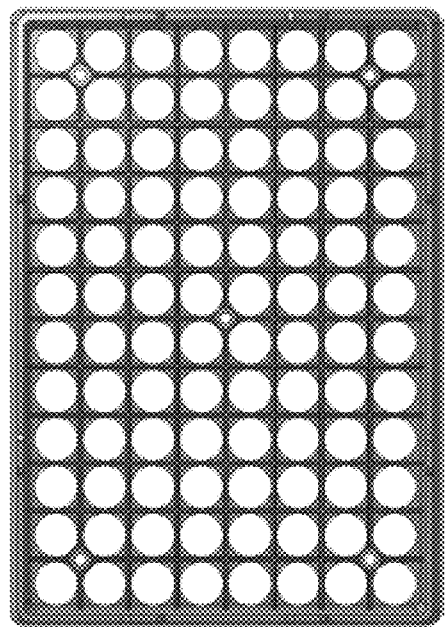
FIG. 8C

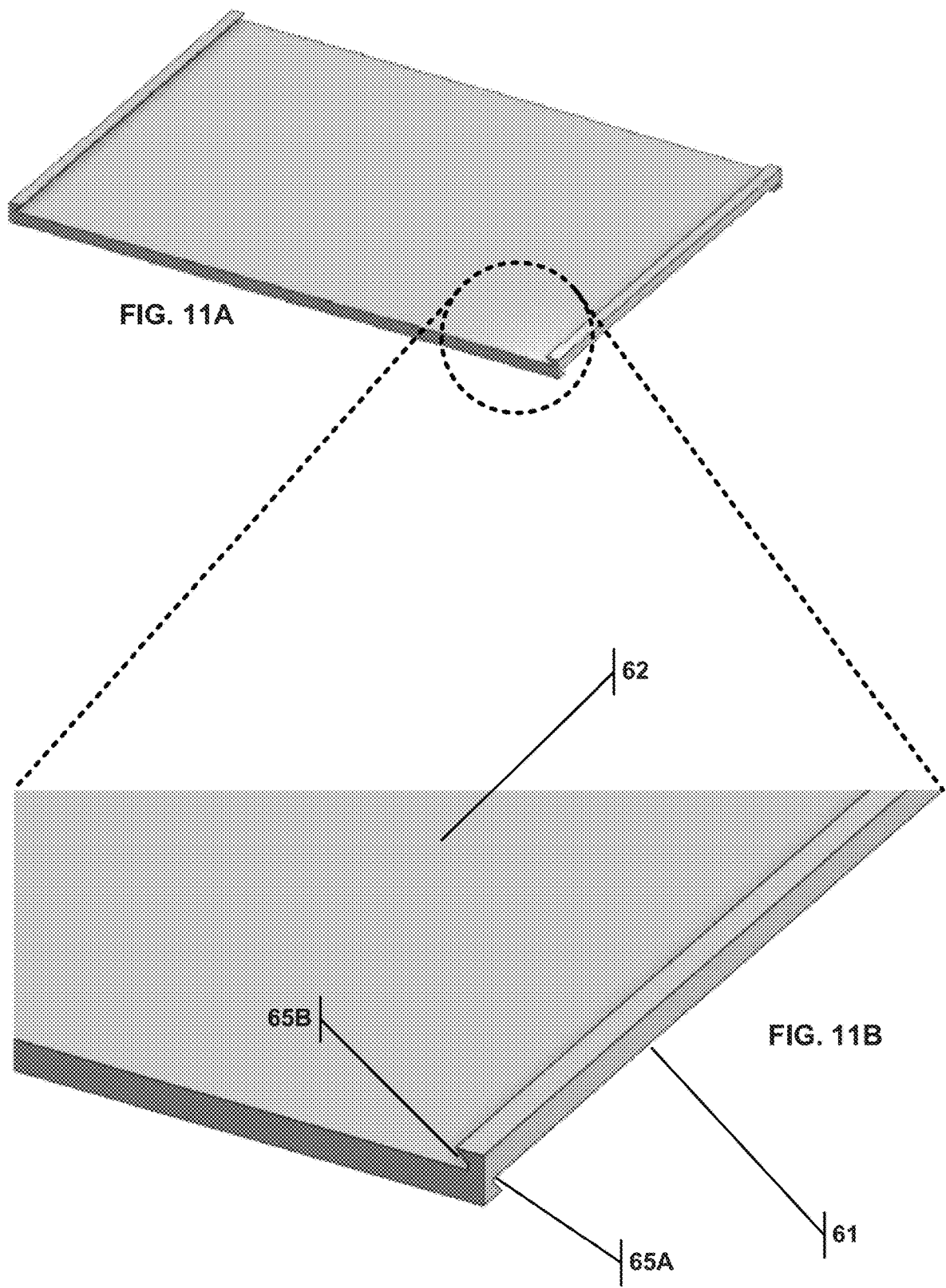

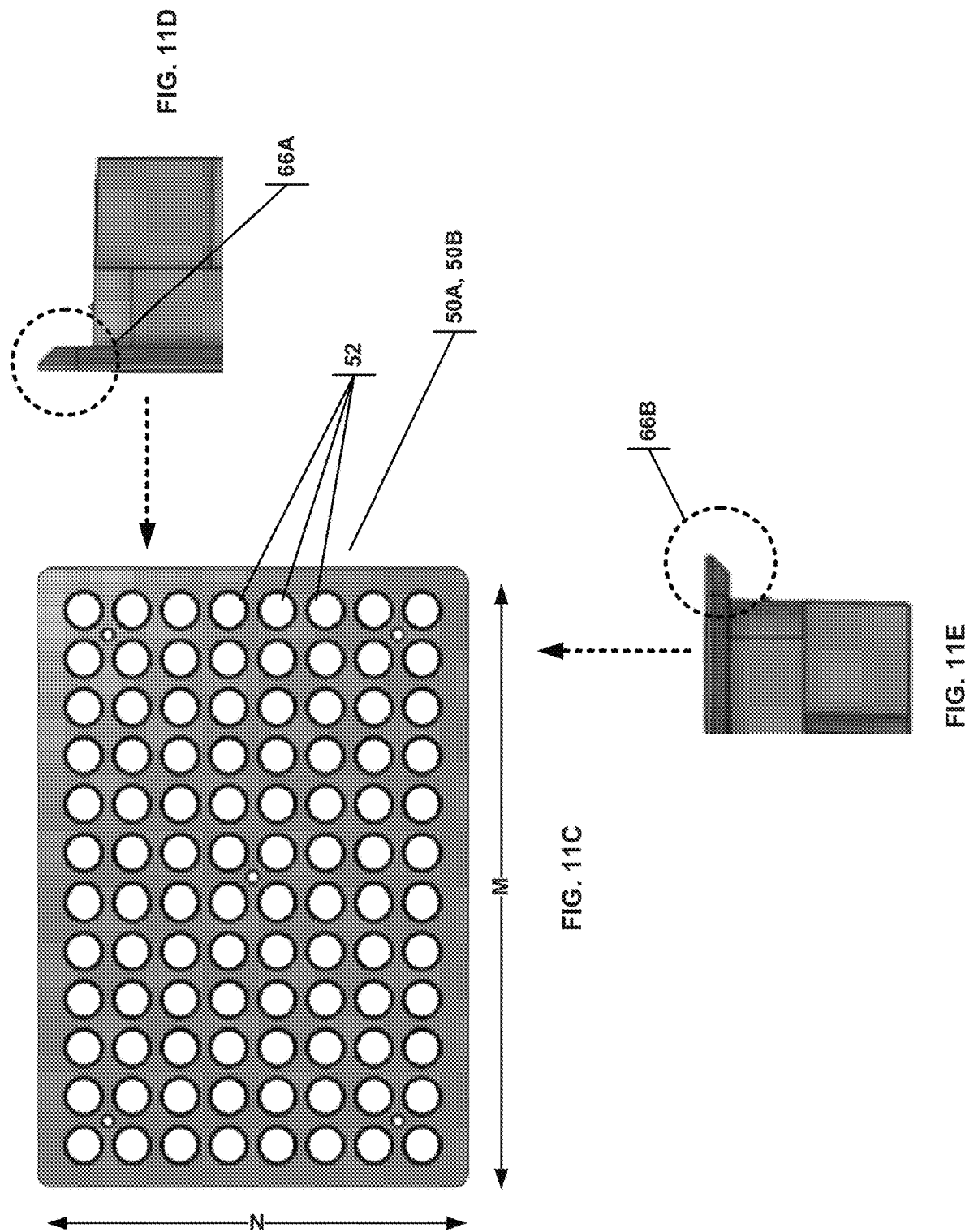

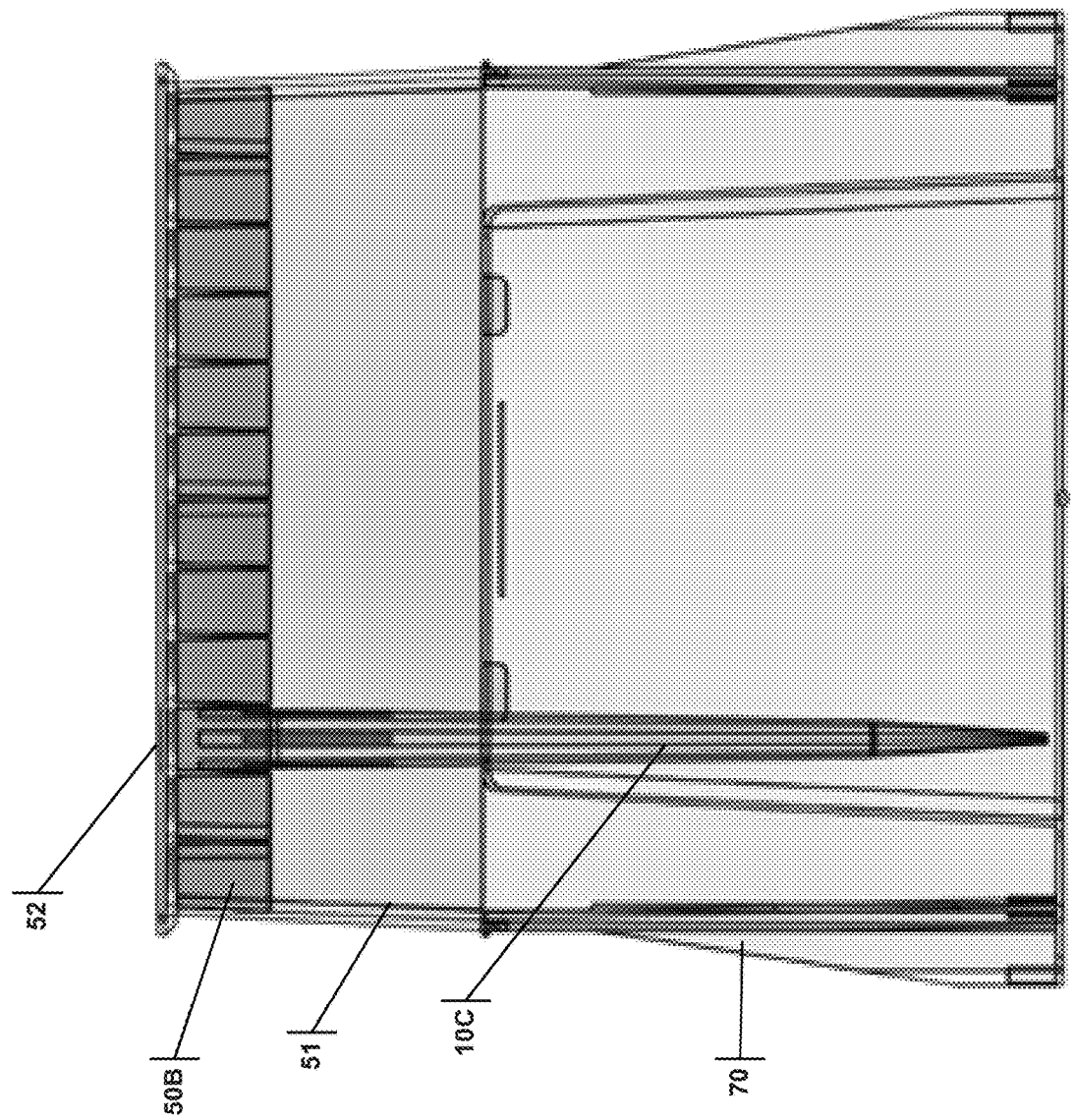

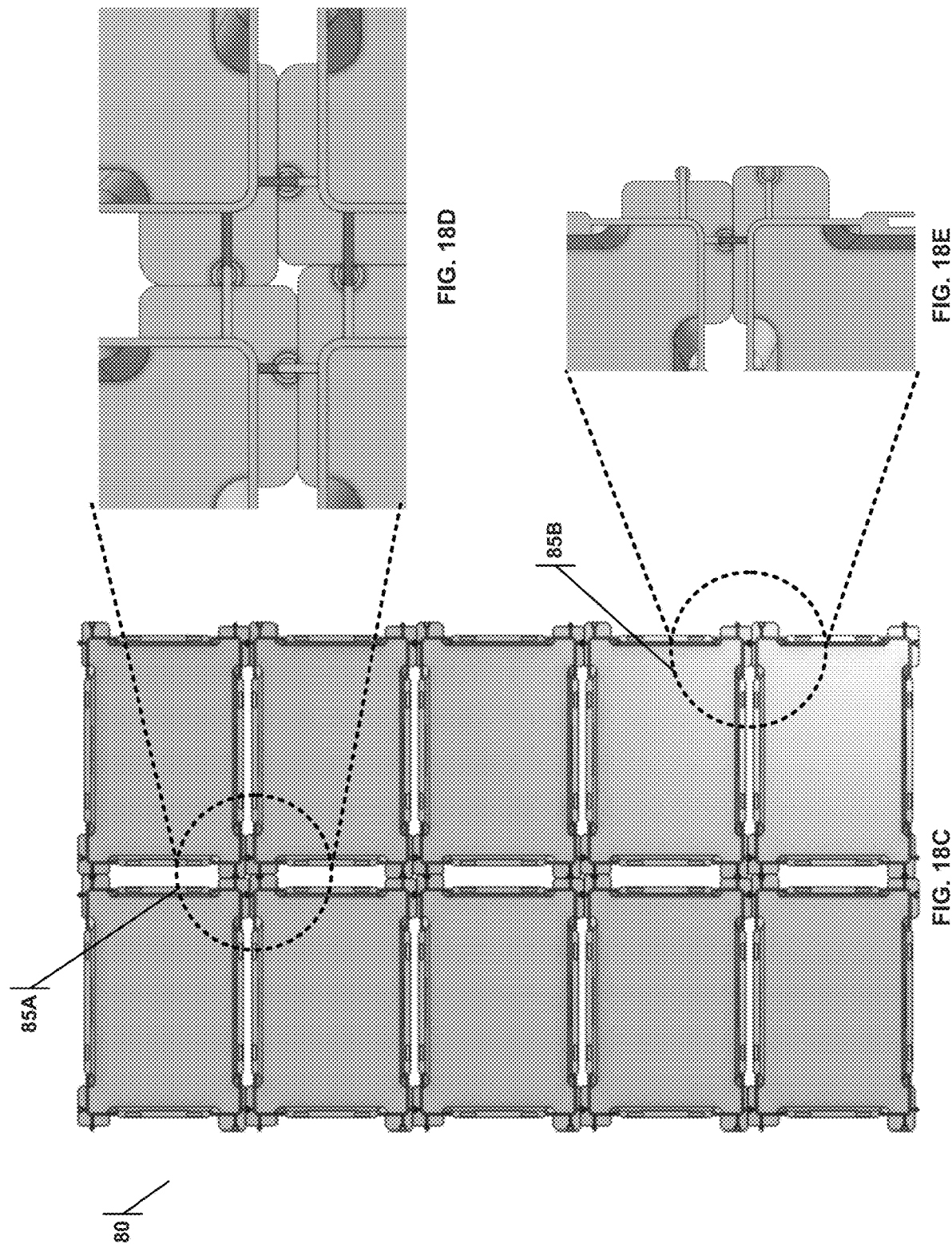

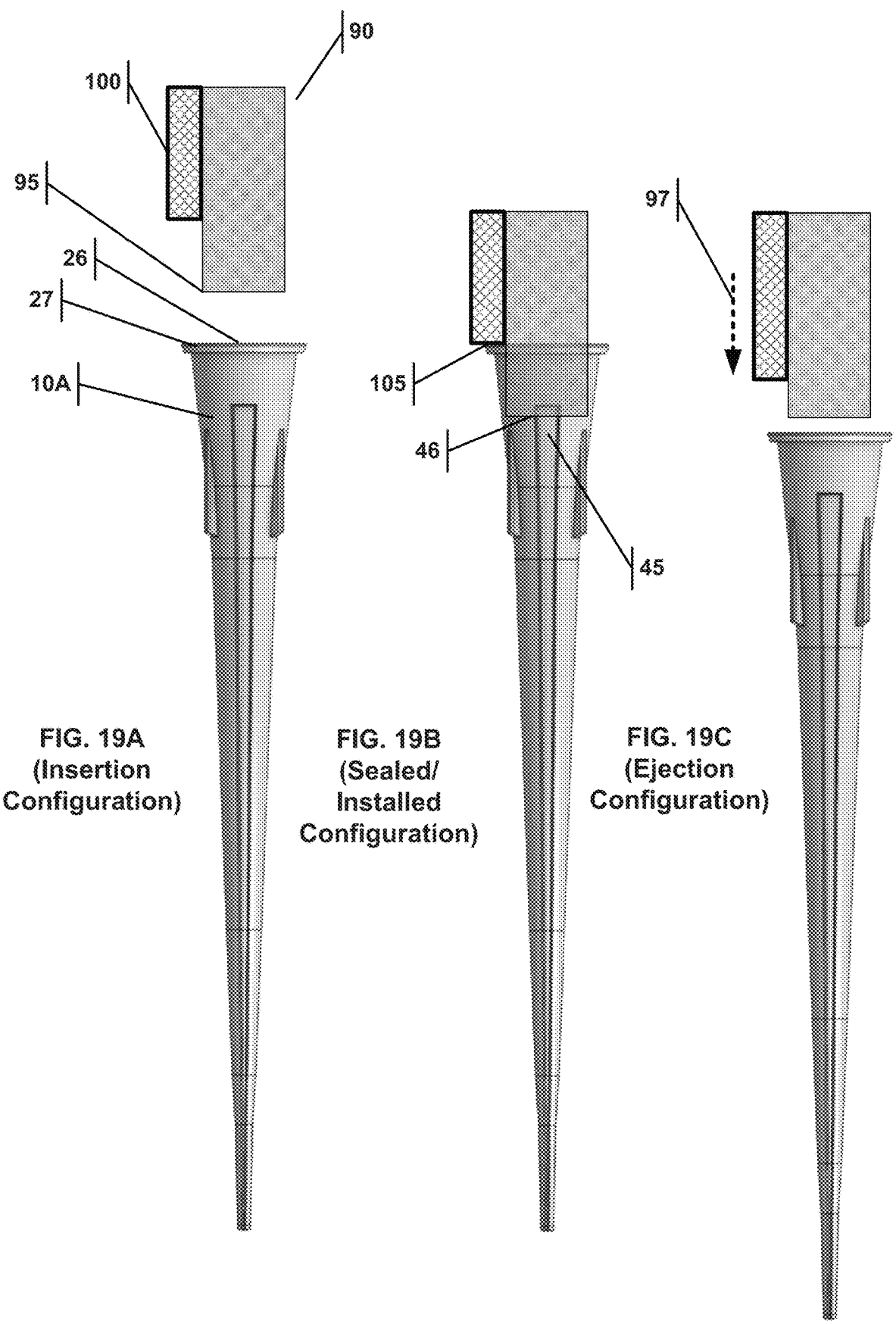
FIG. 19A (Insertion Configuration)   FIG. 19B (Sealed/Installed Configuration)   FIG. 19C (Ejection Configuration)

PIPETTE TIP SYSTEM

1.0 FIELD OF THE INVENTION

This invention relates to pipette tip systems, and more particularly to pipette tips, support cards for the same, lids and pipetters.

2.0 RELATED APPLICATIONS

This application claims priority to provisional application U.S. 63/231,945, filed on Aug. 11, 2021, titled "Pipette Tip System; to provisional application U.S. 63/215,728, filed on Jun. 28, 2021, titled "Pipette Tip System"; and to provisional application U.S. 63/228,081, filed on Jul. 31, 2021, titled "Pipette Tip System". All of these applications are incorporated herein by reference.

3.0 BACKGROUND

Current pipette tips systems have many drawbacks. First, the pipette tip is disposed of in a support card, but is permitted to move significantly within the support card, ultimately rubbing against adjacent tips and building static electricity. This static can misalign the tips, making it more difficult, if not impossible, for a pipetter to accurately mate and seal with the pipette tip.

Second, the pipette tips are shipped in support cards that are individually wrapped and boxed with several of these individually wrapped support cards. During shipping, the individual support cards can jostle against each other, and the pipette tips disposed within each support card and rub against each other, building static electricity. Again, this static misaligns the tips, making it more difficult, if not impossible for a pipetter to accurately mate and seal with the pipette tip.

Third, current support cards maintain the proximal end of the pipette tip proud of the support card top surface—i.e., the pipette tip is over the support card surface. This increases accidents caused by users not lifting the pipette tip sufficiently high enough to clear the adjacent unused pipette tips.

Fourth, current pipette tip systems leave unused pipette tip proximal openings exposed when adjacent tips are being used. This increases the possibility that the unused pipette tips will become inadvertently contaminated.

Fifth, current pipette tip systems do no use a positive stop when mounting the tip to the pipetter. The user just stabs the pipette tip by swinging his or her elbow and forcing the pipette tip onto the pipetter. Without a positive stop, the depth that the pipetter travels into the pipette tip (and, consequently, the force exerted) is not uniform from user to user. When the pipetter tip has accomplished its job, the user presses on a button with his or her thumb, applying a pressure sufficient to dislodge the pipette tip. But because the pipette tip is initially mounted with a large force (sometime upwards of 10-12 lbs.), the user must then apply that level of force, through his or her thumb, to dislodge the pipette tip. Multiplying this action over dozens, if not hundreds of tips in on shift, causes significant user fatigue.

What is needed, therefore, is a system that overcomes these problems.

4.0 SUMMARY

A pipette tip system is disclosed that overcome these shortcomings. In a first embodiment, the system includes a pipette tip with a proximal end that has a rim. The rim defines a proximal opening adapted to receive a pipetter, and the rim includes a rim conical edge. The system also has a support card with a top surface and a pipette tip receiver opening within the top surface, the opening adapted to receive the pipette tip, and wherein the opening has a receiver opening conical edge. The rim conical edge and the receiver conical edge are constructed such that when the pipette tip is disposed of in the pipette tip receiver opening, the rim conical edge abuts the receiver opening conical edge, and the top surface is flush with or nearly flush with the rim.

The top surface may be within +/−0.04 inch of the rim. The rim conical edge may include a first angle, and the receiver opening conical edge may include a second angle, wherein the first angle is complementary to the second angle. The rim may define a rim plane. The rim conical edge may include a first angle, and the a receiver opening conical edge may include a second angle, wherein the first and second angles are selected to assist in the alignment rim plane with the top surface when the pipette tip is disposed of in the pipette tip receiver opening.

In another embodiment, a pipette tip system for use with a plurality of pipette tips is disclosed that includes a support card and a support card lid. The support card includes an array of pipette tip receiver openings arranged in a N×M array, wherein N is less than M. The support card further has a short-side card rail edge on an edge of the support card along the N side of the array, and a long-side card rail edge on an edge of the support card along the M side of the array. The support card lid includes a long-side lid rail edge extending from a support card first surface, which is adapted to slidably mate with the long-side card rail edge, and a short-side lid rail edge extending from a support card second surface, which is adapted to slidably mate with the short-side card rail edge.

The long-side lid rail edge slidably mates with the long-side card rail edge, and the lid may be positioned to expose fewer than all of the pipette receiver openings in the array. The short-side lid rail edge slidably mates with the short-side card rail edge, and the lid may be positioned to expose fewer than all of the pipette receiver openings in the array.

A base may be added that mates with the support card. The support card (50A, 50B) and the base (70) comprise a tongue-and-groove mating system. The base may include an interlocking structure that mates with an adjacent base.

In yet another embodiment, a pipette tip system that includes a pipetter and pipette tip is disclosed. The pipetter has a suction lumen with an opening and an ejection bar that slides relative to the suction lumen. The pipette tip has a distal end with a distal end opening and a proximal end with a rim that defines a proximal opening adapted to receive the pipetter. The pipette tip also has a central lumen extending from the proximal end opening to the distal end opening, and a pipette tip wall extending from the rim and forming the central lumen. The pipette wall comprises a low-force stretch region with a plurality of thinning channels to allow for the stretching of the pipette tip wall. The system comprises at least three configurations: an insertion configuration, wherein (1) the suction lumen (95) is inserted into the proximal opening, and (2) the ejection bar does not abut the rim (27); a sealed/installed configuration, wherein (1) the suction lumen contacts the low-force stretch region, forming a liquid-tight seal between the suction lumen and the pipette wall, and (2) the ejection bar abuts the rim, preventing further insertion of the suction lumen (95); and an ejection configuration, wherein (1) the ejection bar is slid towards the rim with an ejection force, and (2) it dislodges the pipette tip from the suction lumen. The systems may have a plurality of such tips and a support card to support the tips. An improvement of an existing pipetter is also disclosed.

The ejection force may be less than 5 lbs., and the low-force stretch region may be located a distance D from the proximal opening, and the ejection bar is constructed to slide a distance of approximately D relative to the suction lumen.

In yet another embodiment, a pipette tip system for use with a plurality of pipette tips is disclosed that includes a support card connected to a base, wherein the base comprises an interlocking structure constructed to mate with an adjacent base.

Each of the embodiments and feature described herein may be used in combination with each other.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

5.0 BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. Furthermore, various features of different disclosed embodiments can be combined to form additional embodiments, which are part of this disclosure. It will be understood that certain components and details may not appear in the figures to assist in more clearly describing the invention.

FIG. 1A is a side view of a 10 ul pipette tip.
FIG. 1B is a side view of a 10 ul pipette tip of FIG. 1A.
FIG. 1C is a top view of a 10 ul pipette tip of FIG. 1A.
FIG. 1D is a bottom view of a 10 ul pipette tip of FIG. 1A.
FIG. 1E is a side perspective view of a 10 ul pipette tip of FIG. 1A.
FIG. 2A is a side view of a 300 ul pipette tip.
FIG. 2B is a side view of a 300 ul pipette tip of FIG. 2A.
FIG. 2C is a top view of a 300 ul pipette tip of FIG. 2A.
FIG. 2D is a bottom view of a 300 ul pipette tip of FIG. 2A.
FIG. 2E is a side perspective view of a 300 ul pipette tip of FIG. 2A.
FIG. 3A is a side view of a 1200 ul pipette tip.
FIG. 3B is a side view of a 1200 ul pipette tip of FIG. 3A.
FIG. 3C is a top view of a 1200 ul pipette tip of FIG. 3A.
FIG. 3D is a bottom view of a 1200 ul pipette tip of FIG. 3A.
FIG. 3E is a side perspective view of a 1200 ul pipette tip of FIG. 3A.
FIG. 4A is a side perspective view of a pipette tip illustrating the distal end tip.
FIG. 4B is an enlarged view of the distal end tip from FIG. 4A, illustrating the distal end undulating circumference.
FIG. 5A is a side view of a pipette tip illustrating the proximal end.
FIG. 5B is an enlarged view of the proximal end from FIG. 5A, illustrating the proximal end conical edge and the angle of the conical edge.
FIG. 6A is a side view of a pipette tip illustrating a cross-section line 6B-6B.
FIG. 6B is a cross-sectional view taken along line 6B-6B of FIG. 6A, illustrating the anti-nesting ribs and the thinning channels.
FIG. 6C is an enlarged view of the angled distal end of the anti-nesting rib.
FIG. 6D is a side perspective view of a pipette tip.
FIG. 6E is an enlarged view of the conical inside edge constructed to abut the angled end of anti-nesting ribs.
FIG. 6F illustrates one pipette tip nesting into another, with the conical inside edge abutting the angled end of anti-nesting ribs.
FIG. 7A is a top view of a support card (10 ul, 300 ul).
FIG. 7B is the long-side view of the support card (10 ul, 300 ul) of FIG. 7A.
FIG. 7C is a bottom view of the support card (10 ul, 300 ul) of FIG. 7A.
FIG. 7D is the short-side view of the support card (10 ul, 300 ul) of FIG. 7A.
FIG. 7E is a top perspective view of the support card (10 ul, 300 ul) of FIG. 7A.
FIG. 8A is a top view of a support card (1200 ul).
FIG. 8B is the long-side view of the support card (1200 ul) of FIG. 8A.
FIG. 8C is a bottom view of the support card (1200 ul) of FIG. 8A.
FIG. 8D is the short-side view of the support card (1200 ul) of FIG. 8A.
FIG. 8E is a top perspective view of the support card (1200 ul) of FIG. 8A.
FIG. 9A is a top perspective view of a support card and a plurality of pipette tip receiver openings.
FIG. 9B is an enlarged view of one of the pipette tip receiver openings from FIG. 9A, illustrating the receiver opening conical edge.
FIG. 9C illustrates a pipette tip disposed of in the pipette tip receiver opening of the support card, where the top surface of the support card is flush or nearly flush with the pipette rim.
FIG. 9D illustrates a side view of the rim plane and the top surface of the support card.
FIG. 9E illustrates an enlarged view of FIG. 9D, showing the rim plane and the top surface of the support card.
FIG. 9F illustrates the prior art, wherein the proximal end of the pipette tips protrudes above the support card top surface.
FIG. 10A is a top view of a support card lid.
FIG. 10B is the long-side view of the support card lid of FIG. 10A.
FIG. 10C is a bottom view of the support card lid of FIG. 10A.
FIG. 10D is the short-side view of the support card lid of FIG. 10A.
FIG. 10E is a top perspective view of the support card lid of FIG. 10A.
FIG. 11A is a top perspective view of the support card lid.
FIG. 11B is an enlarged view of the corner of the support card lid of FIG. 11A, illustrating the long-side lid rail edge and the short-side lid rail edge.
FIG. 11C is a top view of the support card.
FIG. 11D is an enlarged side view of the support card of FIG. 11C, illustrating the support card rail edge (long side).
FIG. 11E is an enlarged side view of the support card of FIG. 11C, illustrating the support card rail edge (short side).
FIG. 12A illustrates the card lid installed on the support card and slid open to expose two rows of tip receiver openings (a total of 16 exposed).

FIG. 17 is a cross-sectional view of the support card (1200 ul) installed on the base with a 1200 ul pipette tip disposed in the pipette tip receiver opening of the support card.

FIG. 18C illustrates an array of bases (10) interlocked with one another, with an interlocking region highlighted.

FIG. 18D is an enlarged view of the four-base interlocking region of FIG. 18C.

FIG. 18E is an enlarged view of the two-base interlocking region of FIG. 18C.

FIG. 19A illustrates a pipette tip system in an insertion configuration.

FIG. 19B illustrates the pipette tip system in a sealed/installed configuration, wherein the top rim of the pipette tip abuts the ejection bar, causing a positive stop.

FIG. 19C illustrates the pipette tip system in an ejection configuration, where the sliding movement of the ejection bar relative to the suction lumen pushes on the top rim of the pipette tip and dislodges/ejects the pipette tip from the pipetter.

6.0 DETAILED DESCRIPTION

Figure 1A:
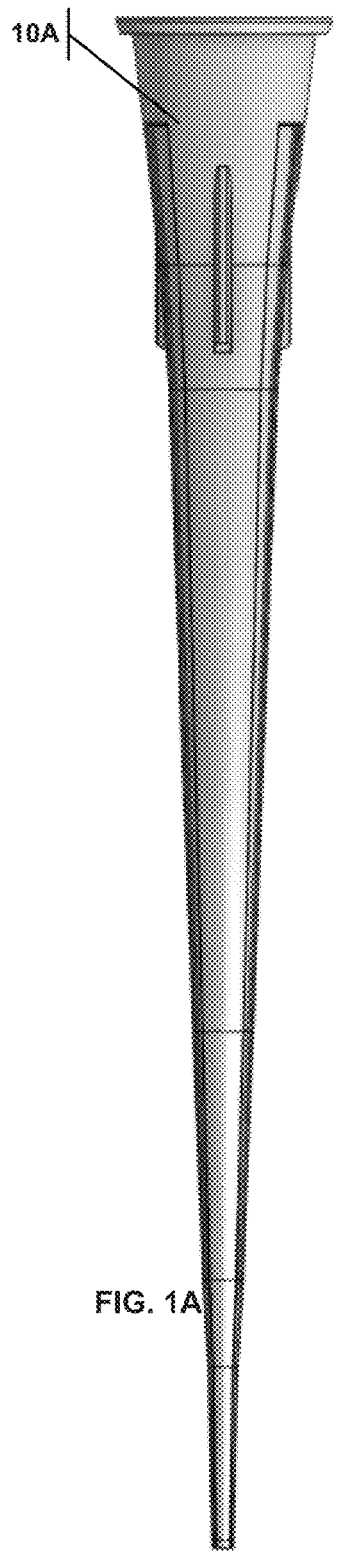
Figure 1B:
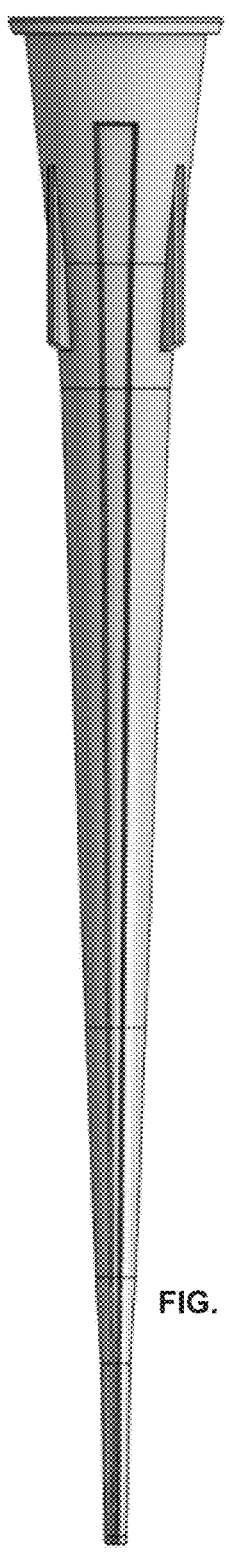
Figure 1C:
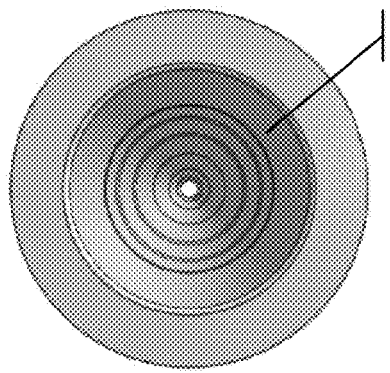
Figure 1D:
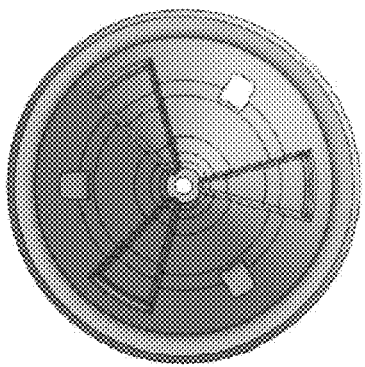
Figure 1E:
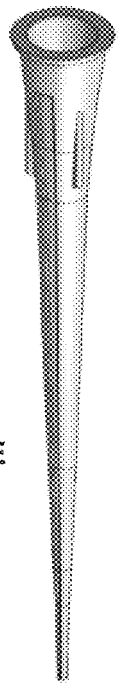
Figure 2A:
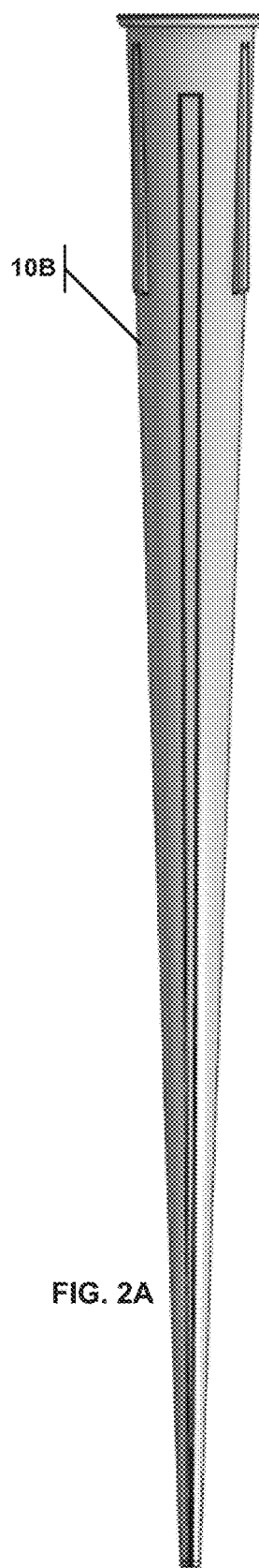
Figure 2B:
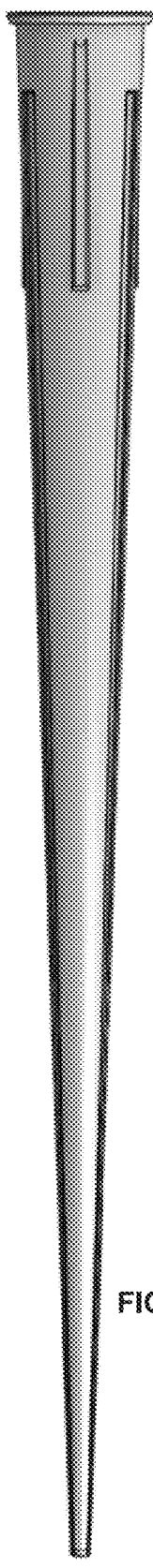
Figure 2C:
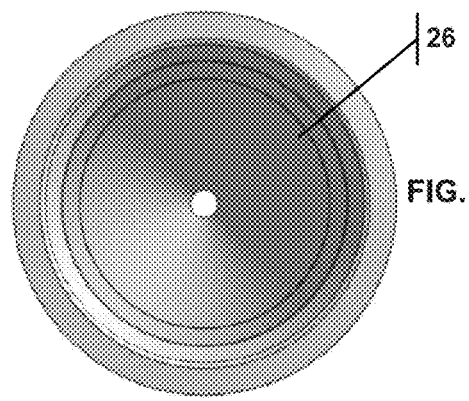
Figure 2D:
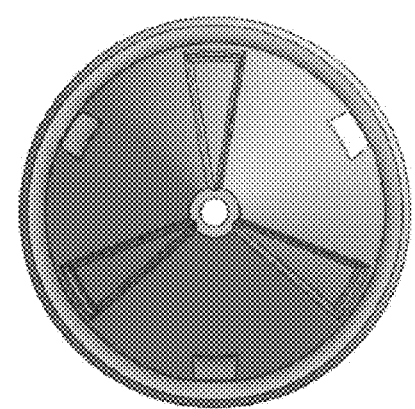
Figure 2E:
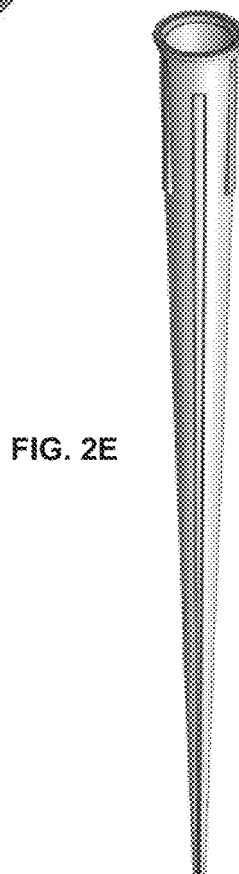

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents, as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well-known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms, unless noted otherwise. Similarly, various steps of the methods shown and described herein are not necessarily performed in the order indicated, or performed at all, in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated, connection does not necessarily mean a direct, unimpeded connection, unless otherwise noted.

The following list of example features corresponds to the attached figures and is provided for ease of reference, where like reference numerals designate corresponding features throughout the specification and figures:

Pipette Tip (10 ul Extra Large) 10A
Pipette Tip (300 ul) 10B
Pipette Tip (1200 ul) 10C
Pipette Tip Distal End 15
Distal End Opening 16
Central Lumen 17
Central Lumen Axis 18
Conical Body 19
Distal End Undulating Circumference 20
Pipette Tip Proximal End 25
Proximal End Opening 26
Pipette Tip Rim 27
Rim Plane 27-1
Proximal End Conical Edge 30
Angle of Conical Edge 35
Shelf 36
Conical Body Angle 37
Anti-Nesting Ribs 40
Angled End of Anti-Nesting Ribs 41
Conical Inside Edge 42
Thinning Channels 45
Low-Force Stretch Region 46
Support Card (10 ul, 300 ul) 50A
Support Card (1200 ul) 50B
Tall Apron 51
Plurality of Pipette Tip Receiver Openings 52
Receiver Opening Conical Edge 55
Angle of Receiver Opening Conical Edge 55-1
Transition Conical Edge 57
Support Card Top Surface 56
Support Card Lid 60
Support Card Lid First Surface 61

Support Card Lid Second Surface 62
Lid Rail Edge (long-side) 65A
Lid Rail Edge (short-side) 65B
Support Card Rail Edge (long-side) 66A
Support Card Rail Edge (short-side) 66B
Base 70
Support Card Protrusion 71
Base Floor 70-1
Base Protrusion Receiver Slot 72
Support Card Tab 73
Base Tab Receiver Slot 74
Base Interlocking Male Key 75A
Base Interlocking Female Key 75B
Interlocked Array of Bases 80
Four-Base Interlocking Region 85A
Two-Base Interlocking Region 85B
Pipetter 90
Pipetter Suction Lumen 95
Pipetter Ejection Bar 100
Positive Stop 105
Existing Pipetter 109
Ejection Bar Distal Edge 110

The present invention presents many embodiments and many aspects that may be used independently or in conjunction. FIGS. 1A-1E illustrate various views of a pipette tip 10A with a volume of 10 ul, FIGS. 2A-2E illustrate various views of a pipette tip 10B with a volume of 300 ul, and FIGS. 3A-3E illustrate various views of a pipette tip 10C with a volume of 1200 ul.

Each of these pipette tips (10A, 10B, 10C) may have a pipette distal end 15 with an undulating circumference 20, as shown in FIGS. 4A and 4B. This circumference 20 serves many purposes. For example, the undulated design keeps the pipette tip more straight and rigid, and allows the drop from the pipette distal end to evacuate (dislodge) more effectively. In prior designs, the distal ends may bend because they are not sufficiently rigid. When operating the pipetter with prior tip designs, the distal end would cling to a drop of the pipette fluid, and that drop could dislodge during the movement of the pipette tip, contaminating the work area. An undulating circumference 20 lowers the surface tension at the distal end 15 and discourages the distal end from clinging to the pipette fluid.

Figures 5A, 5B:
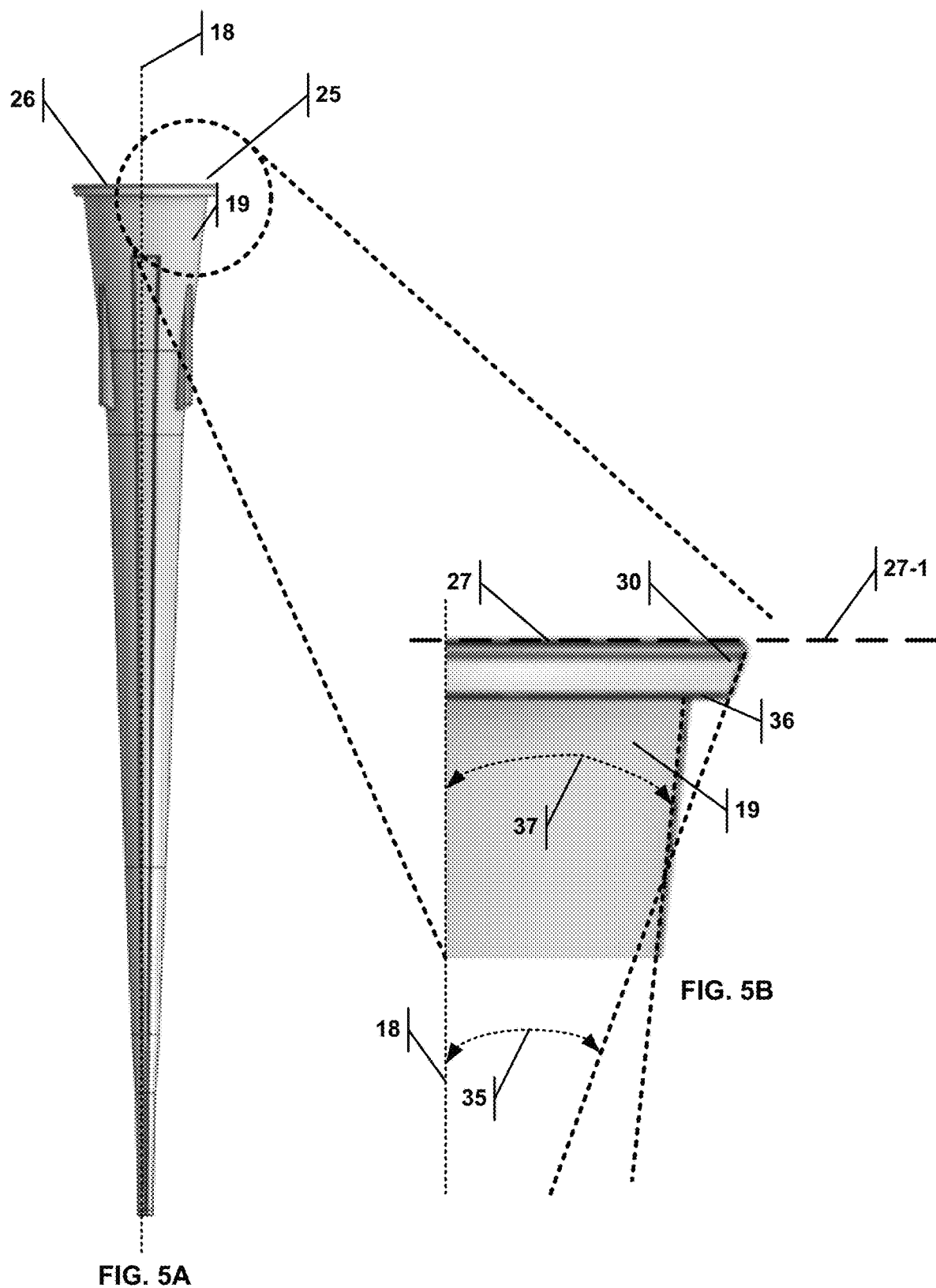
Figure 9A:
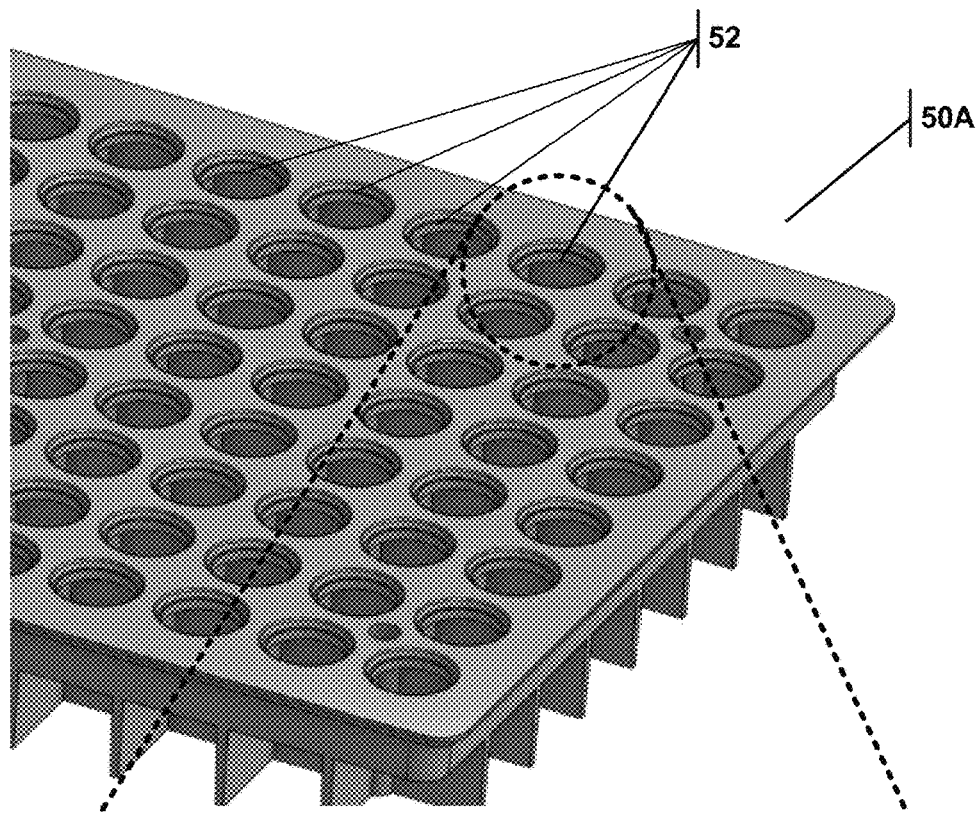
Figure 9B:
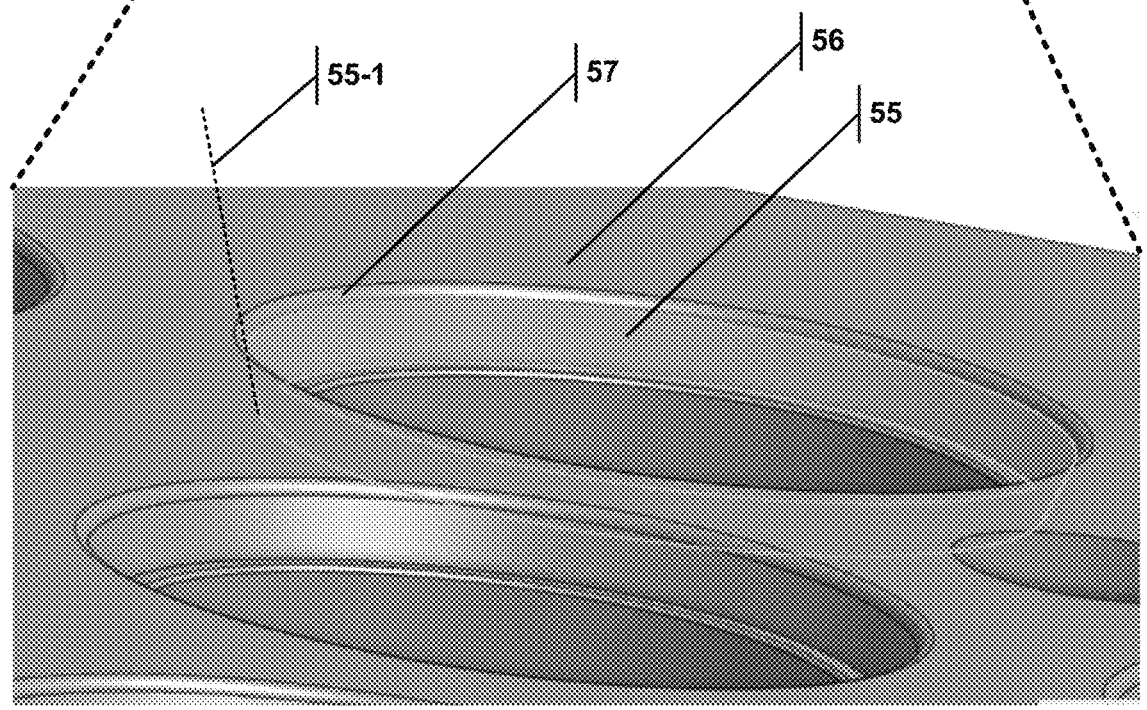
Figure 12A:
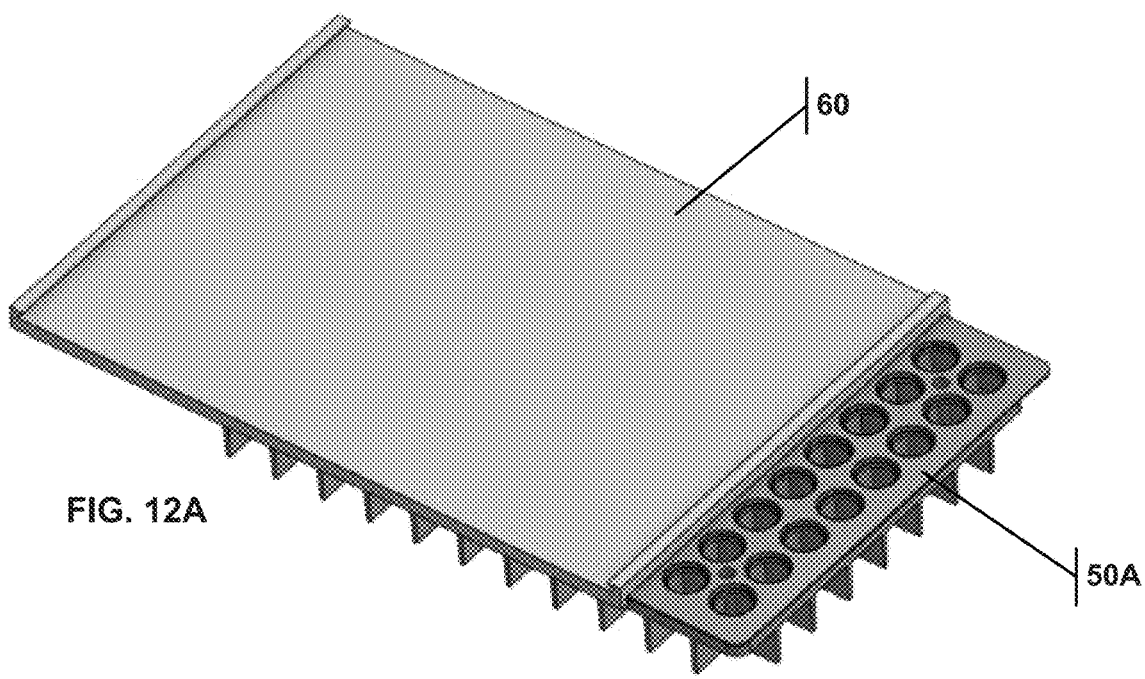
FIG. 12B illustrates the card lid installed on the support card (90 degrees from the installation shown in FIG. 12A) and slid open to expose two rows of tip receiver openings (a total of 24 exposed).
Figure 12B:
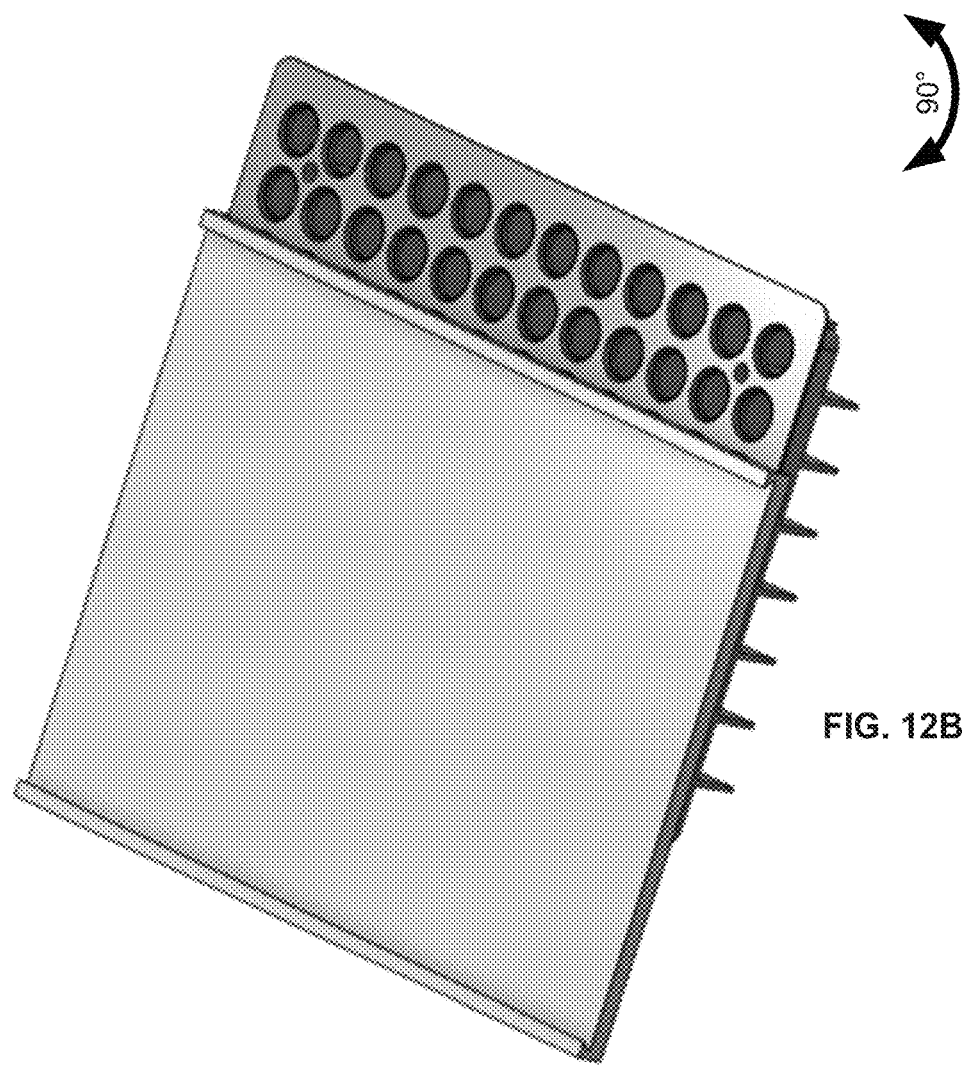
Figure 13A:
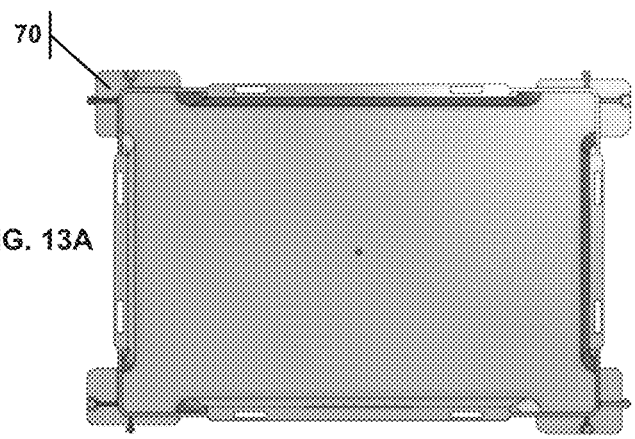
FIG. 13A is a top view of a base.
Figure 13D:
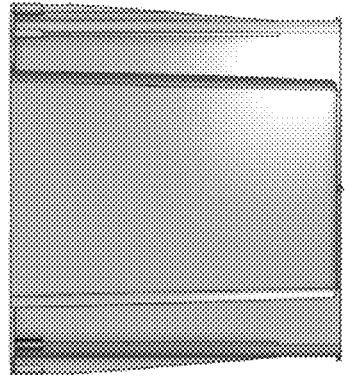
FIG. 13D is the short- side view of the base of FIG. 13A.
Figure 13B:
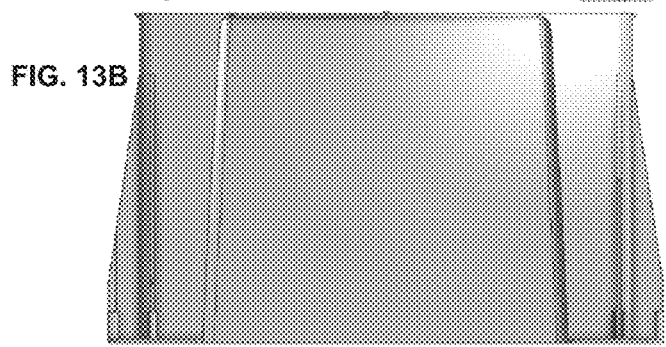
FIG. 13B is the long-side view of the base of FIG. 13A.
Figure 13C:
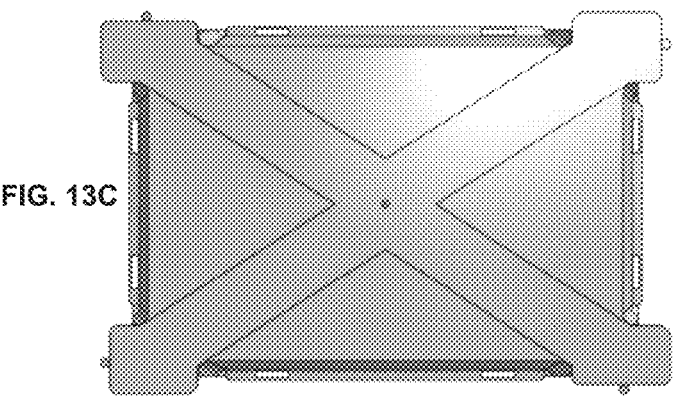
FIG. 13C is a bottom view of the base of FIG. 13A.
Figure 13E:
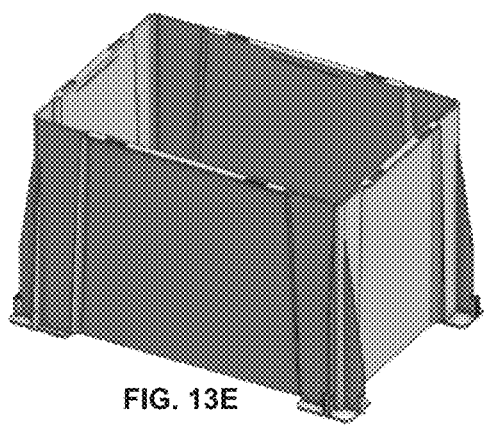
FIG. 13E is a top perspective view of the base of FIG. 13A.

Each of these pipette tips (10A, 10B, 10C) may have a pipette tip proximal end 25 with a proximal end opening 26, and a rim 27 with a conical edge 30. The proximal end opening 26 connects to the distal end opening 16, through a central lumen 17 (see FIG. 4A). The central lumen 17 defines a central lumen axis 18. As shown in FIGS. 5A and 5B, the conical edge 30 has an edge angle 35 that is complementary to the receiver opening conical edge angle 55-1 (FIG. 9B) of the pipette tip receiver openings 52 (FIG. 9A) in the support card 50A. The receiver opening conical edge 55 may also have a transition conical edge 57 formed into the support card top surface 56 and extending away from the top surface 56. When the pipette tip (10A, 10B, 10C) is disposed of in the pipette tip receiver opening 52 of the support card 50A, the top surface of the support card 56 is preferably flush with the pipette tip rim 27. When the support card lid 60 is installed on the support card (50A, 50B), as shown in FIGS. 12A and 12B, the flushness of the pipette tip rim 27 to the top surface of the support card 56 maintains the pipette tips substantially fixed relative to the support card (50A, 50B), so that the tips do not rub against adjacent pipette tips when the support card (50A, 50B) is handled, which avoids creating static electricity that then misaligns the pipette tips. Given manufacturing tolerances, it may not be precisely flush. Within +/−0.04 of an inch of flush would be preferable.

The complementary conical edges (30, 55) self-align the pipette tip (10A, 10B, 10C) into the pipette tip receiver opening 52, stabilizing the pipette tip and preventing the pipette tip from rubbing against adjacent pipette tips and creating static electricity. Alignment means that the pipette tip (10A, 10B, 10C) is plumb in the pipette tip receiver opening 52, such that the distal ends of the pipette tips in the support card (50A, 50B) do not contact one another. The pipette tip rim 27 defines a rim plane 27-1 (see FIG. 5B) that is aligned with the top surface of the support card (56). The rim plane 27-1 is substantially parallel to the top surface of the support card (56).

The build-up of static electricity causes the proximal ends of the pipette tips to attract one another, thereby misaligning the proximal ends of the tips. This misalignment can prevent an automated pipetter from properly inserting and sealing into the pipette tips.

Figure 9C:
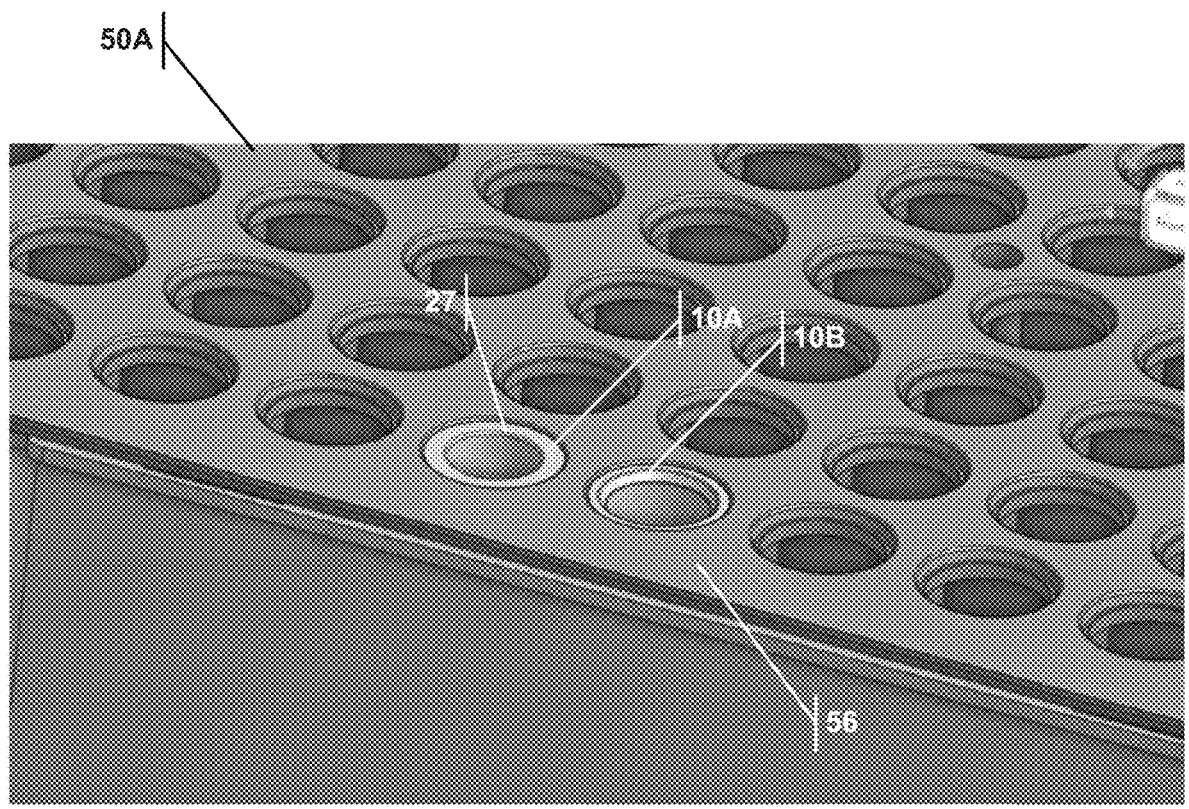
Figure 9D:
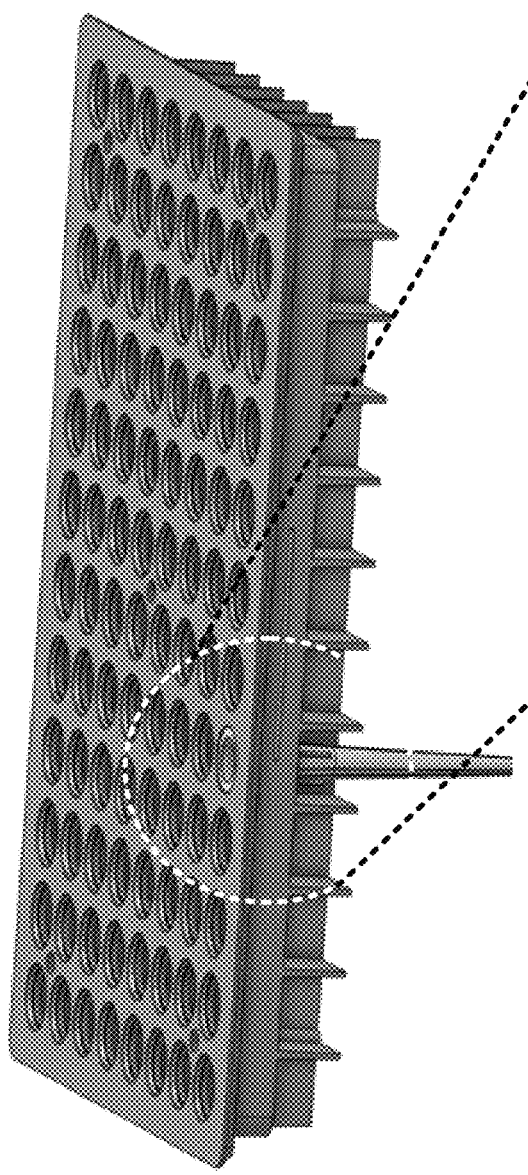
Figure 9E:
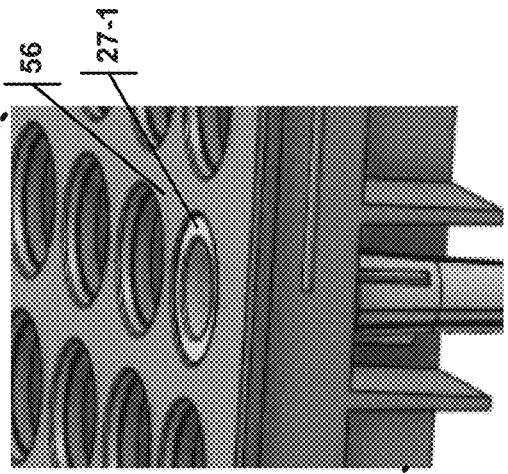
Figure 9F:
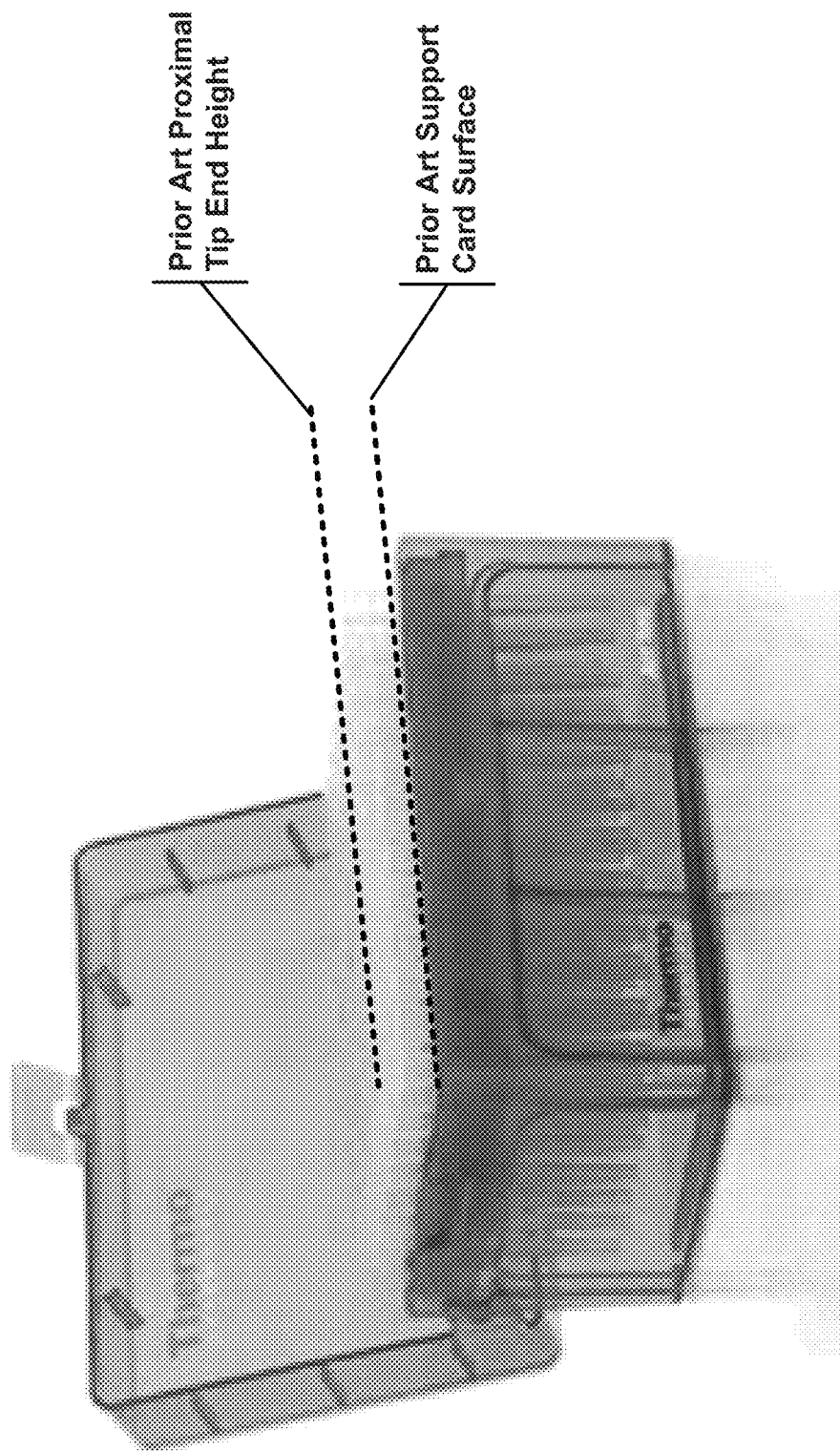
Figure 10A:
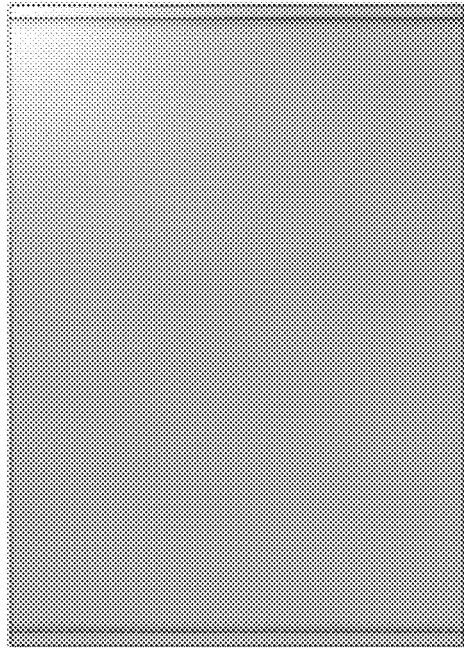
Figure 10B:
Figure 10C:
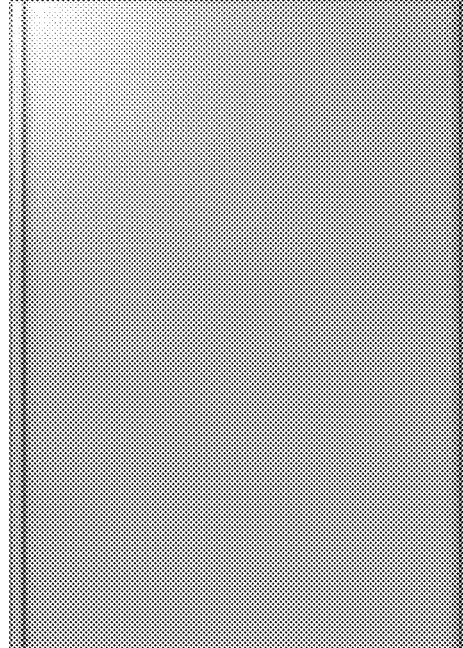
Figure 10D:
Figure 10E:
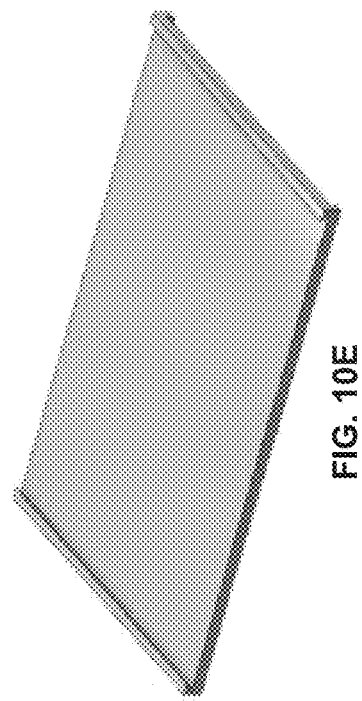

Having the proximal end of the pipette tip flush or nearly flush with the support card surface has the additional benefit of reducing the likelihood of knocking over the support card filled with pipette tips. Specifically, when a user accesses a pipette tip and installs it on a pipetter, the user then lifts the pipetter with the tip attached. If, as in prior art designs, the proximal ends of the pipette tips stand proud of the support card surface (i.e., protrude past the support card surface), as shown in FIG. 9F, the user may not lift the distal end of the pipette tip enough and may inadvertently hit one of the adjacent pipette tips that is protruding from the support card surface. This can cause the entire support card to be knocked over, potentially contaminating the unused pipette tips.

In the current design, since the rim of the pipette tip is flush, or nearly flush with the support card surface (see FIG. 9C), the user must lift the pipetter tip distal end higher than the support card surface (56), and will therefore be clear of any adjacent tips at that height. FIGS. 9D and 9E illustrate a side view of the rim plane 27-1 compared to the top surface of the support card 56. The difference between the current design of the present invention (9C, 9D) and the prior art (9F) is readily seen by comparing the Figures. In contrast with prior art, there is no substantial proximal tip end height that extends up over the support card top surface (56).

Figures 6A, 6B, 6C:
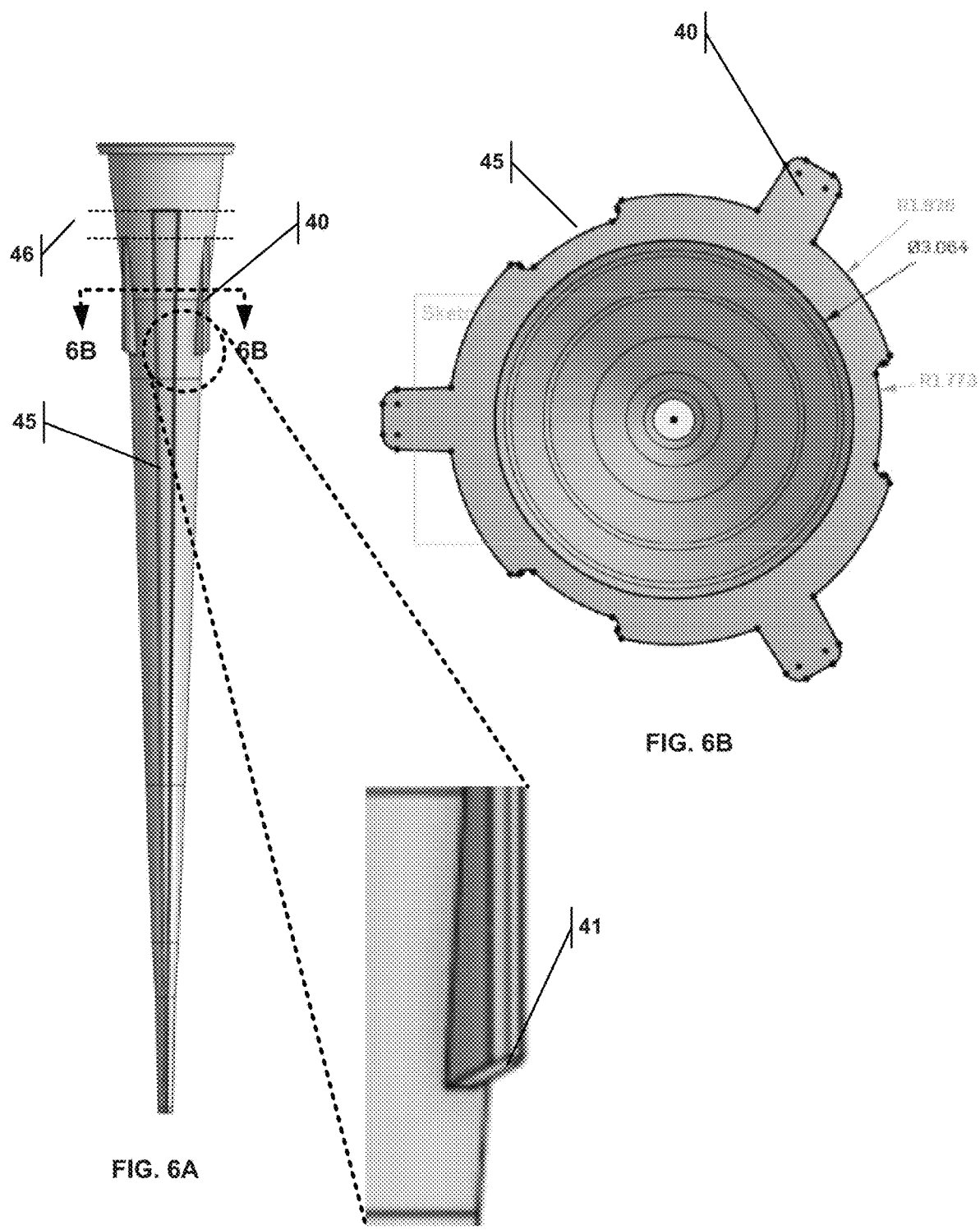

Each of these pipette tips (10A, 10B, 10C) may have a cross-section as shown in FIGS. 6A and 6B. Specifically, the pipette tips may include thinning channels 45 and anti-nesting ribs 40. The pipette walls extending from the pipette tip rim 27 towards the distal end form the central lumen 17 and include a low-force-stretch region 46.

When a user jabs and dislodges hundreds of tips during a shift, user fatigue becomes a major issue. Lowering the force (i.e., strength) necessary to accomplish these functions will lower fatigue.

A thinning channel 45 is a portion of the pipette tip wall that is thinner than the other portions of the wall, which allows the pipetter to more easily seal onto the pipette tip because the wall at the thinning channel 45 will allow the pipette tip (10A, 10B, 10C) to stretch more easily around the pipetter 90. This feature can help with user fatigue, because the force necessary to form a proper seal when jabbing the pipetter 90 onto the pipette tips (10A, 10B, 10C) is reduced compared with prior art, as is the force necessary to dislodge the pipette tip (10A, 10B, 10C) from the pipetter 90 when the pipette tip (10A, 10B, 10C) is no longer needed.

Figure 6D:
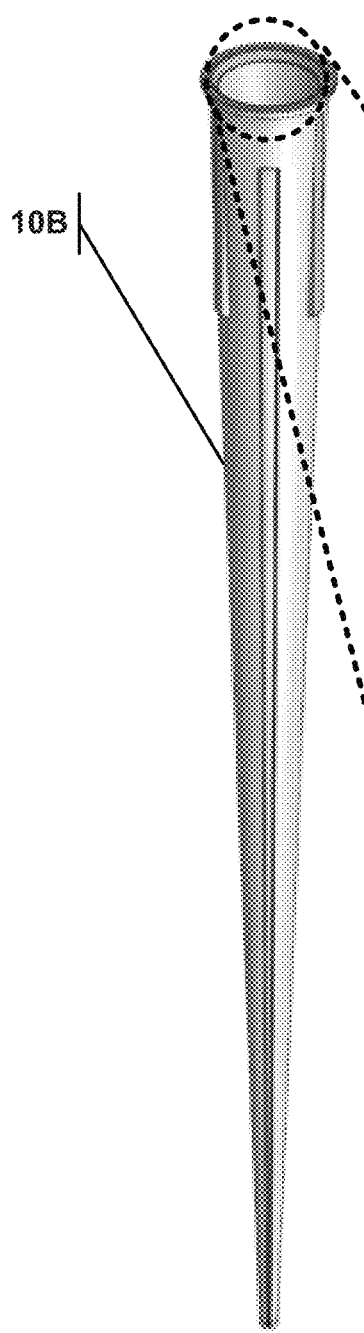
Figure 6E:
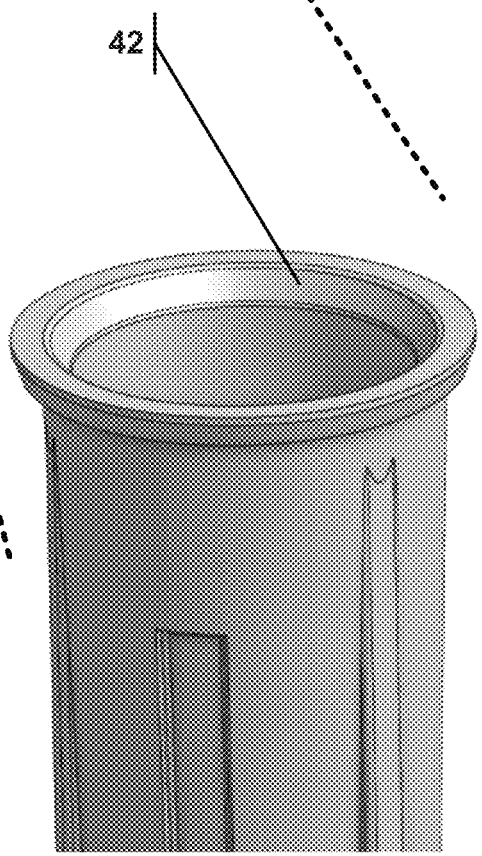
Figure 6F:
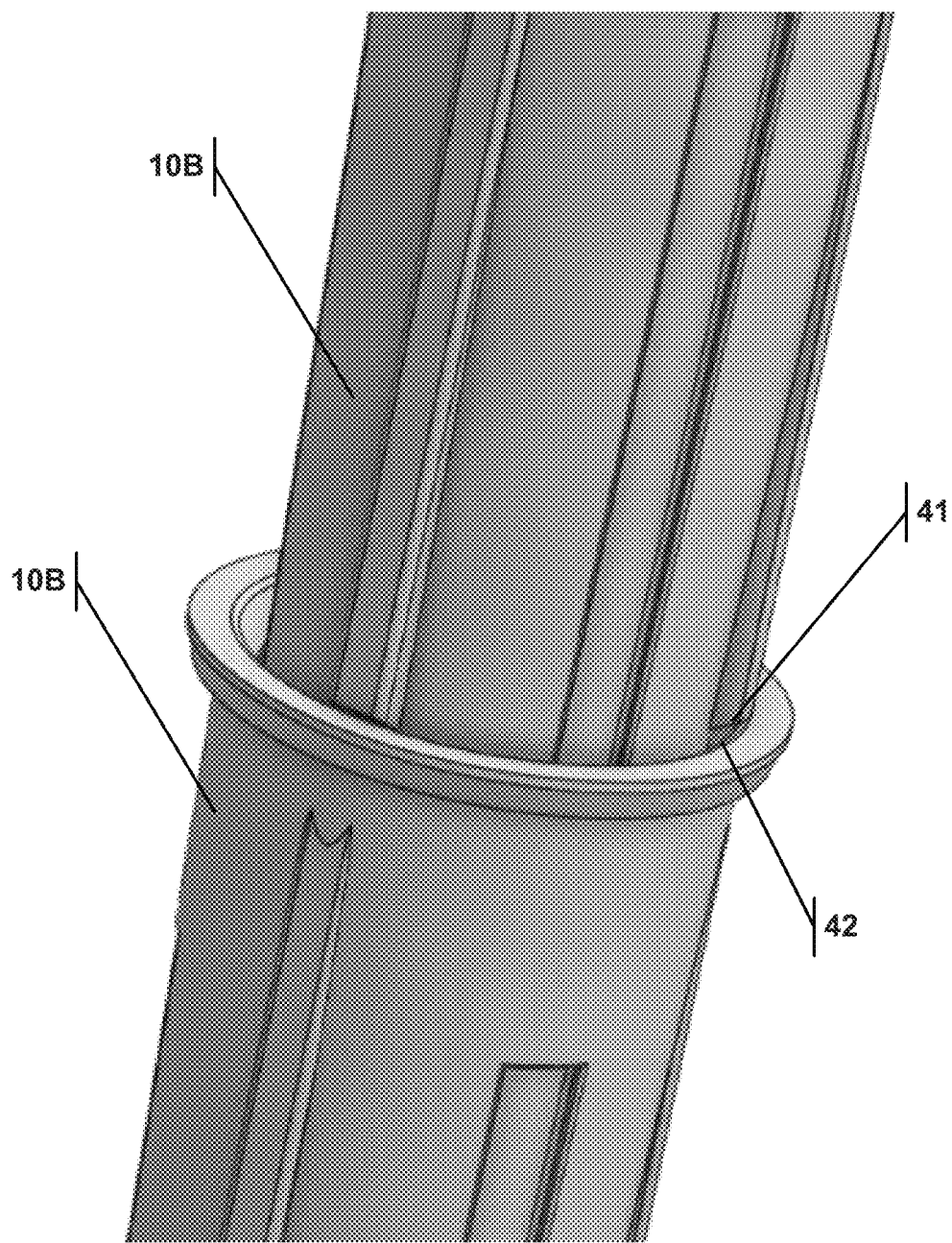

The anti-nesting ribs 40 prevent an upper pipette tip from sticking to a lower pipette tip, allowing the top pipette tip to be easily removed. The anti-nesting ribs 40 also have a slight angle 41, and the proximal end of the pipette tip may have a conical inside edge 42 that abuts the angle 41 and allows the top pipette tip to self-align when it is partially inserted into a bottom pipette tip. This is shown in FIGS. 6D-6F.

FIGS. 7A-7E illustrate various view of a support card 50A for use with pipette tips (10A, 10B). FIGS. 8A-8E illustrate various view of a support card 50B for use with pipette tip 10C. Support card 50B has larger diameter pipette receiver openings than those of card 50A, and it has a tall apron 51; both of these features allow support card 50B to accommodate the larger 1200 ul pipette tip 10C. Both support cards (50A and 50B) have the receiver opening conical edge 55 to allow the pipette tip (10A, 10B, 10C) to lie flush or nearly flush with the top surface of the support card (50A, 50B) (see FIGS. 9A-9C).

A lid is shown in FIGS. 10A-10E in various views. This lid can be used with either support card (50A, 50B). FIGS. 11A and 11B illustrate a unique structure on the lid—i.e., a lid rail edge (long-side) 65A extending from a support card lid first surface 61 and a lid rail edge (short-side) 65B extending from a support card lid second surface 62.

The support card (50A, 50B) has complementary structures—a support card rail edge (long-side) 66A and a support card rail edge (short-side) 66B, as shown in FIGS. 11C-11E. As shown in FIG. 11C, the support card (50A, 50B) pipetter tip receiver openings (52) are arranged in a N×M array, wherein N is less than M, the support card (50A, 50B). The lid rail edge (long-side) 65A runs along the M side of the array and can engage the support card rail edge (long-side) 66A, as shown in FIG. 12A, allowing a single short row or multiple short rows to be exposed, depending on the position of the lid 60 relative to the support card (50A, 50B). Alternatively, the lid 60 can be flipped, and the lid rail edge (short-side) 65B that runs along the N side of the array can engage the support card rail edge (short-side) 66B, as shown in FIG. 12B, allowing a single long row or multiple long rows to be exposed, again depending on the position of the lid 60 relative to the support card (50A, 50B). Limiting the exposure of the pipette tips to only those rows needing to be uncovered prevents the uncovered and unused pipette tips from becoming contaminated. Also, the unique design of the lid 60 and support cards (50A, 50B) permits the use of multi-pipetters, which generally allows the simultaneous loading of a row of 8 or 12 pipette tips.

Figure 14:
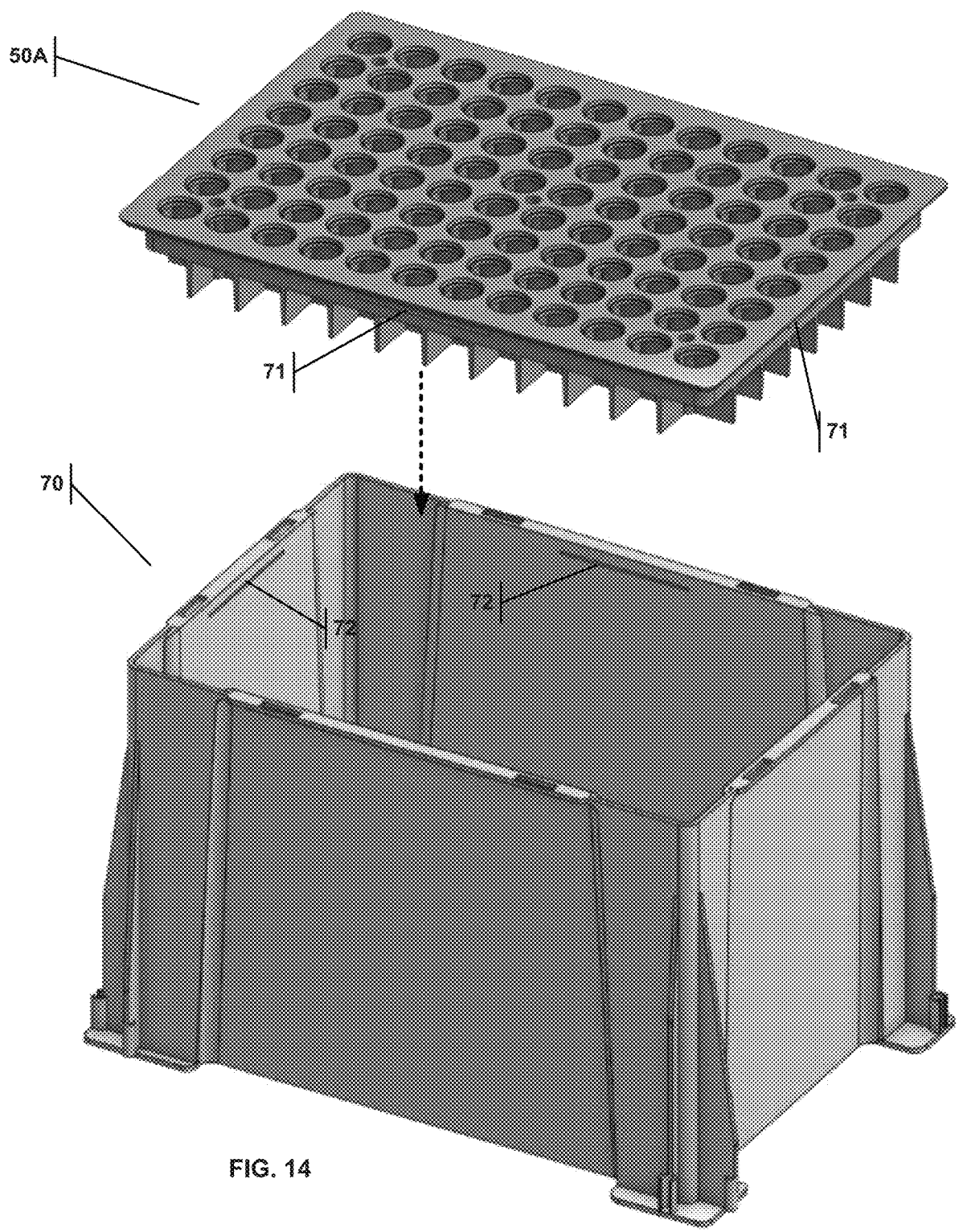
FIG. 14 illustrates the installation of the support card (10 ul, 300 ul) to the base, wherein the support card protrusion inserts into the base protrusion receiver slot.
Figure 15:
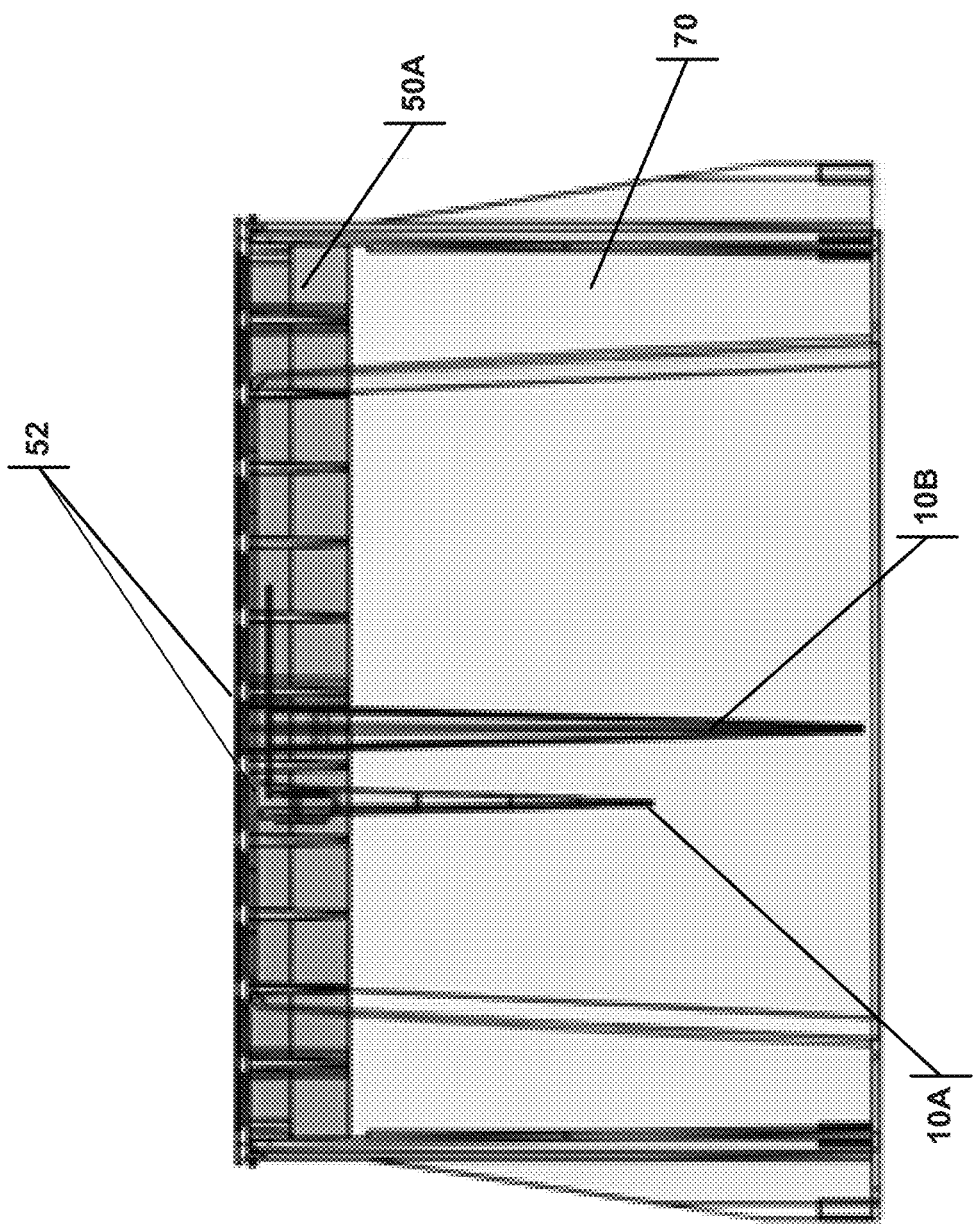
FIG. 15 is a cross-sectional view of the support card (10 ul, 300 ul) installed on the base with both a 10 ul pipette tip and a 300 ul pipette tip disposed in the pipette tip receiver opening of the support card.
Figure 16:
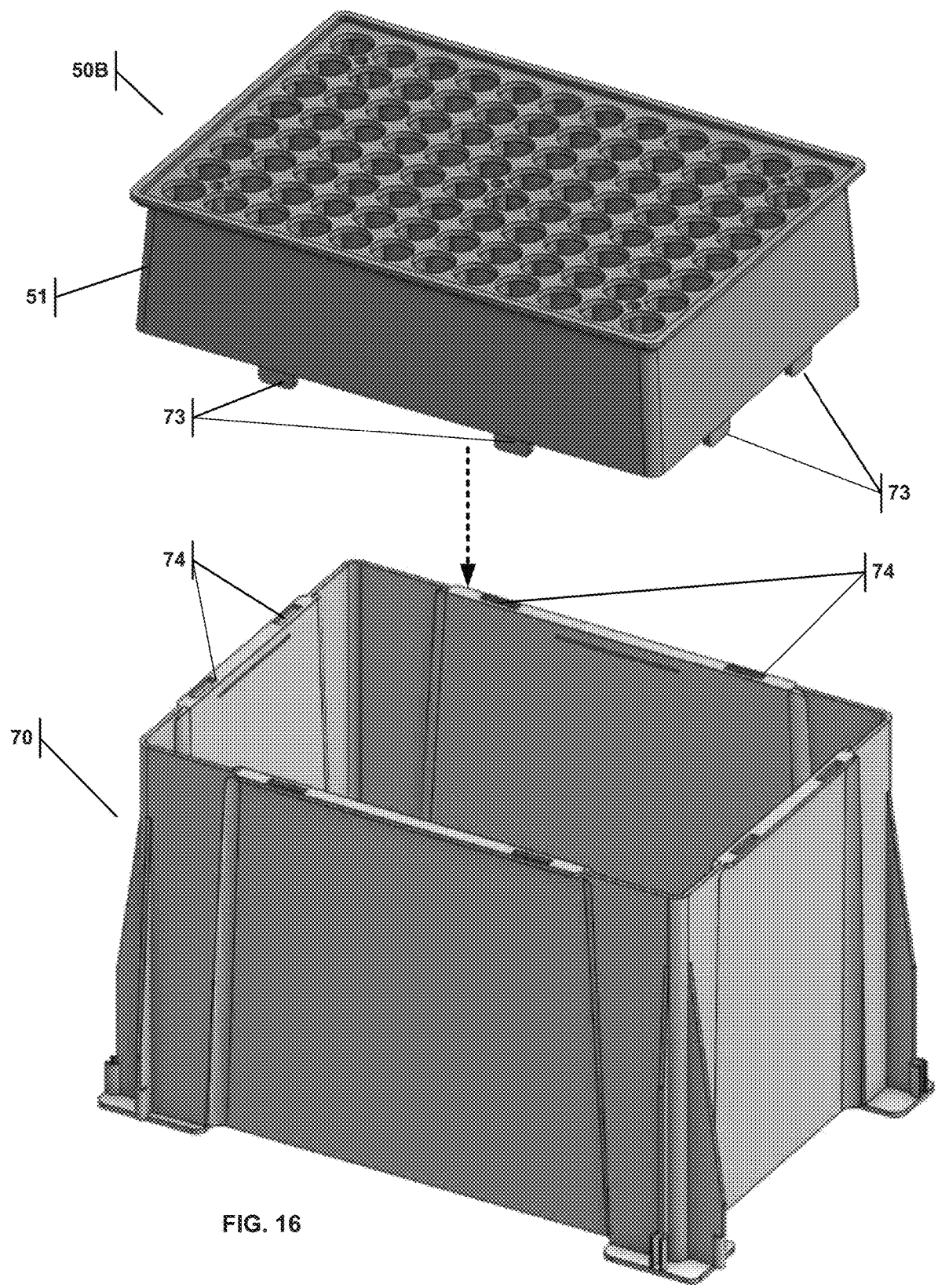
FIG. 16 illustrates the installation of the support card (1200 ul) to the base, wherein the support card tab inserts into the base tab receiver slot.

FIGS. 13A-13E illustrate the base 70 with a base floor 70-1 that may be used with either support card 50A or 50B, and any one of the sizes of pipette tips (10A, 10B, 10C). FIG. 14 illustrates a support card 50A mating with a base 70, using support card protrusions 71 that mate with base protrusion receiver slots 72. Shown in FIG. 15 is a see-through view of the support card 50A mated with the base 70, and two differently sized pipette tips (10A, 10B) disposed of in the pipette tip receiver openings 52 of the support card 50A. The support card 50A suspends the pipette tips (10A, 10B) above the base floor 70-1. FIG. 16 illustrates a support card 50B mating with a base 70, this time using support card tabs 73 on the support card 50B that insert into the base tab receiver slots 74 on the base 70. Of course, the protrusion 71 could be instead on the base 70 and the receiver slot 72 on the support card 50A, which would be an obvious variation without departing from the scope of the present invention. Likewise, the tab 73 could instead be on the base 70, and the slot 74 could instead be on the support card 50B, without departing from the present invention. This is more generally referred to as a tongue-and-groove mating system.

Shown in FIG. 17 is a see-through view of the support card 50B mated with base 70, and a pipette tip 10C disposed of in a pipette tip receiver opening 52 of the support card 50B. It should be noted that the pipette tip receiver openings 52 of support card 50B are larger than those of support card 50A, which requires the tall apron 51 to mount on top of the base to accommodate the larger diameters of the pipette tip receiver openings 52 and the corresponding larger diameters of the pipette tip 10C.

Figure 18A:
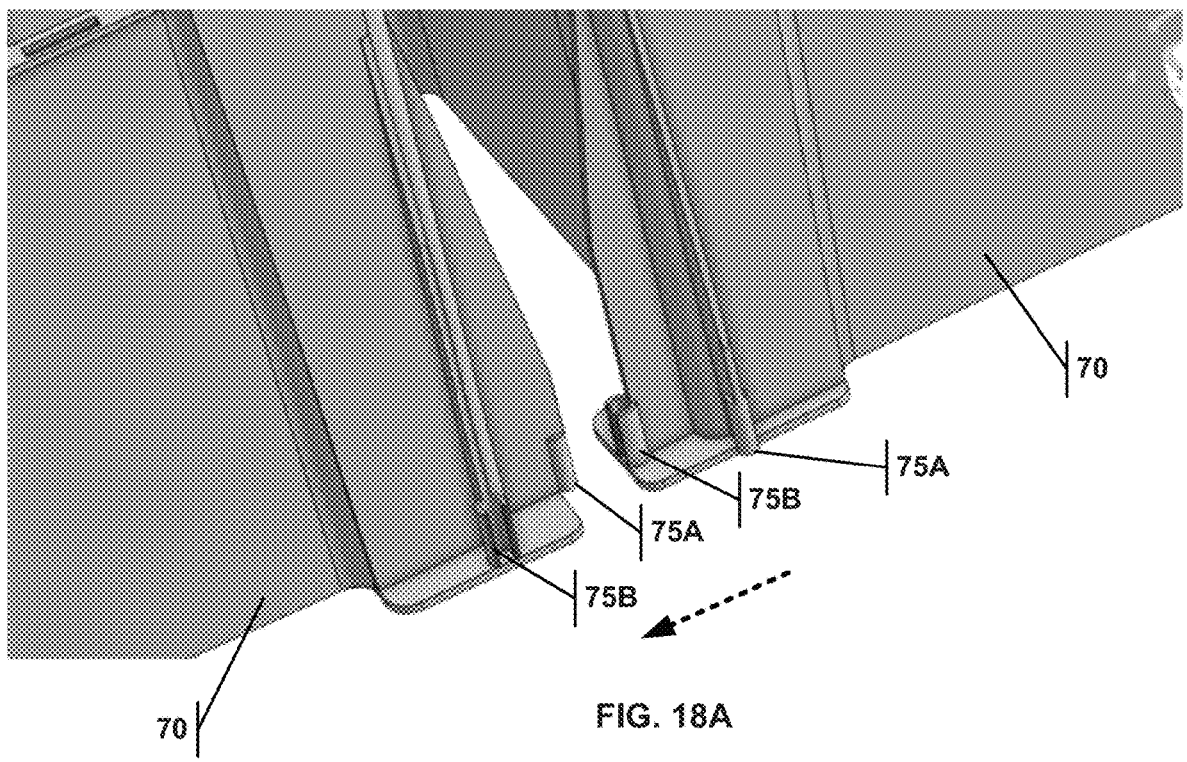
FIG. 18A illustrates two adjacent bases, each base with a base-interlocking male key and a base-interlocking female key.
Figure 18B:
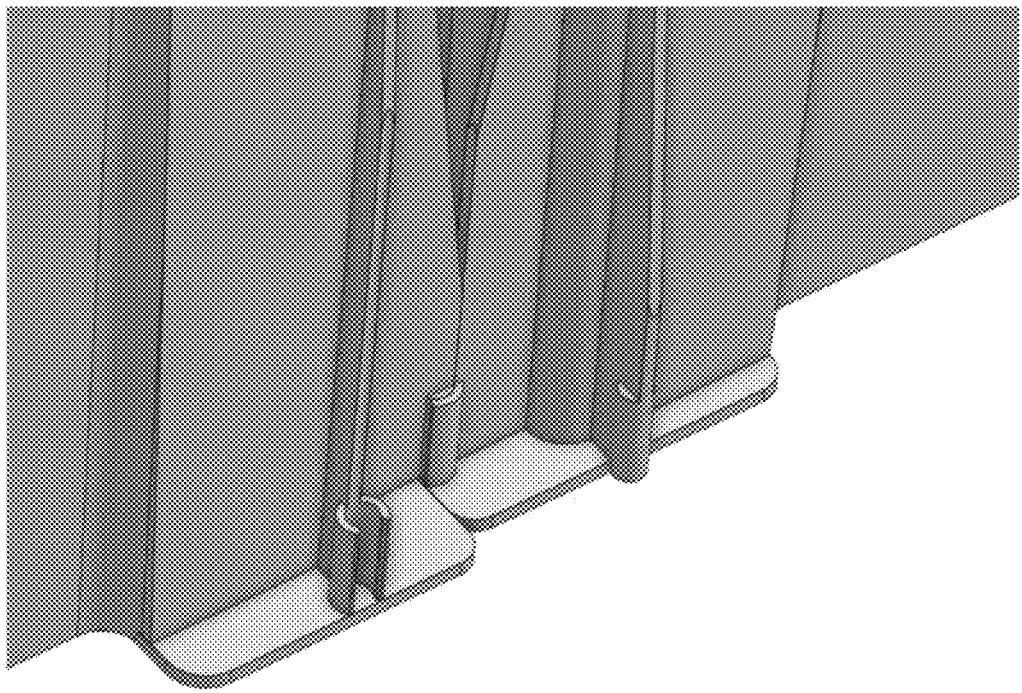
FIG. 18B illustrates two bases interlocked with one another by use of the base-interlocking male key from one base interlocked with the base-interlocking female key from the other base.

FIG. 18A illustrates the use of the base interlocking male key 75A on one base 70 and the base-interlocking female key 75B on an adjacent base 70, and the mating of those structures to interlock the bases 70 with one another, as shown in FIG. 18B. Each corner on the base may include both a base-interlocking male key 75A and a base-interlocking female key 75B, such that an array 80 of bases may be interlocked, with a four-base interlocking region 85A and a two-base interlocking region 85B (FIGS. 18D and 18E). In practice, there may be a second support card connected to a second base, wherein the second base includes a second interlocking structure that can interlock with an adjacent base. As shown in FIG. 18C, ten bases are interlocked together to form a single structure. Although not shown, each of the bases in FIG. 18C, may be connected to a support card, and pipette tips may be disposed of in the support cards.

Currently, pipette tips are loaded into a support card, and the card is individually packaged in a box, and several boxes are wrapped in a heat-shrink seal. This is a tremendous amount of wasteful packaging, and the heat-shrink wrap often has static that makes it difficult to fully unwrap prior to use. This individual base packaging is necessary to prevent the bases from shifting during shipping or cutting into the packaging, thus comprising their sterility. But by having the bases 70 interlock, the pipette tips can be more efficiently shipped and handled. An array of bases 80 can be interlocked and loaded with pipette tips, and the entire array can be sealed using a hermetically sealed bag. The user can open the bag, separate one of the bases containing pipette tips, and re-seal the unused tips. Since the bases are interlocked, they will not shift relative to one another during shipping and handling. Also, the corners of the base 70 are rounded to prevent the base from cutting the packaging during shipping.

FIGS. 19A-19C illustrate the positive stop features of the present system. First, FIG. 19A illustrates the system in an insertion configuration, where the pipetter 90 is locating and is approaching the top proximal opening of the pipette tip 10A. The pipetter 90 has a suction lumen 95 that inserts into the top proximal opening 26 of the pipette tip, and an ejection bar 100 that can be engaged to slide relative to the suction lumen 95 (shown by arrow 97) to push against the top rim 27 of the pipette tip to dislodge and to eject the pipette tip 10A from the pipetter 90. In the insertion configuration, (1) the suction lumen 95 is inserted into the proximal opening 26, and (2) the ejection bar 100 does not abut the rim 27 because it is in the unengaged position.

Next, FIG. 19B illustrates the sealed/installed configuration, where the pipette tip 10A is installed and sealed on the pipetter suction lumen 95, wherein the top rim 27 of the pipette tip 10A abuts the ejection bar 100, causing a positive stop 105. In other words, the pipetter 90 cannot be inserted further into the pipette tip 10A. Preferably, the suction lumen 95 would be inserted a sufficient distance into the pipette tip 10A to reach the thinning channel 45. Recall that these channels 45 are a portion of the pipette tip wall's low-force stretch region 46 that is thinner than the other portions of the wall, allowing the pipetter 90 to more easily seal onto the pipette tip 10A because the wall 46 at the thinning channel 45 will allow the pipette tip 10A to stretch more easily around the pipetter 90. This feature can help with user fatigue, because the force necessary to form a proper seal when jabbing the pipetter 90 onto the pipette tips 90A is lowered, as is the force necessary to dislodge the pipette tip 10A from the pipetter 90 when the pipette tip 10A is no longer needed.

After the pipette tip 10A has served its purpose, FIG. 19C illustrates the ejection configuration, where the user engages the ejection bar 100 by pressing a button that causes the ejection bar to slide relative to the suction lumen (in the direction of arrow 97) towards the rim 27, pushing on the rim 27 and thereby dislodging/ejecting the pipette tip 10A from the suction lumen 95 of the pipetter 90.

In prior art designs, a user could jab the pipetter into the pipette tip with a strong force (this is generally accomplished by bending the user's arm, so the strong force is easy to attain). However, when the pipette tips needs to be ejected, a correspondingly strong force is needed, but the force is accomplished by pushing a button with the user's thumb. Sometime 10 or 12 lbs. of pressure is needed to dislodge and to eject the pipette tip in prior art systems. This will quickly cause user fatigue.

Because the present system has a positive stop 105 and preferably uses thinning channels 45, it can be designed to have a constant seal force and a constant ejection force, both of which can be lower compared to the prior art systems, thereby reducing user fatigue. As a non-limiting example, a force of less than 5 lbs. can both seal and eject the pipette tips, and more preferably a force of less than 2 lbs. is needed.

Figure 20A:
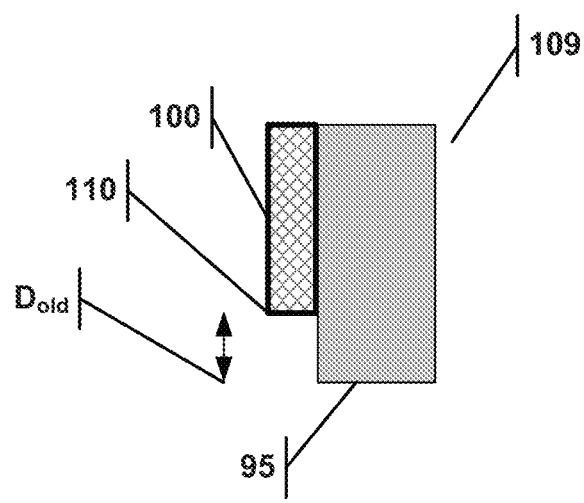
FIG. 20A illustrates the potential shortcomings of using existing pipetters that do not use an ejection bar positioned at the correct distance to form an optimal seal.
Figure 20B:
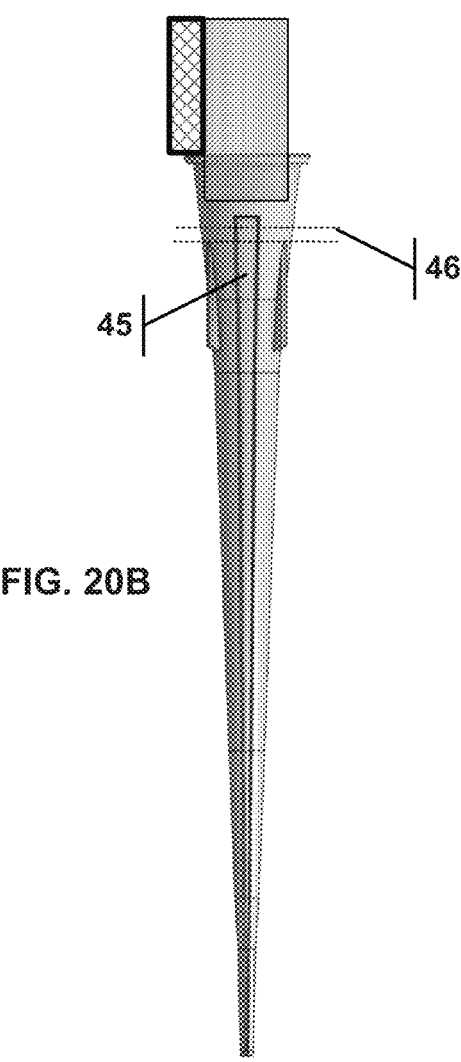
FIG. 20B illustrates a potential shortcoming of using existing pipetters that do not use an ejection bar positioned at the correct distance to form an optimal seal.
Figure 20C:
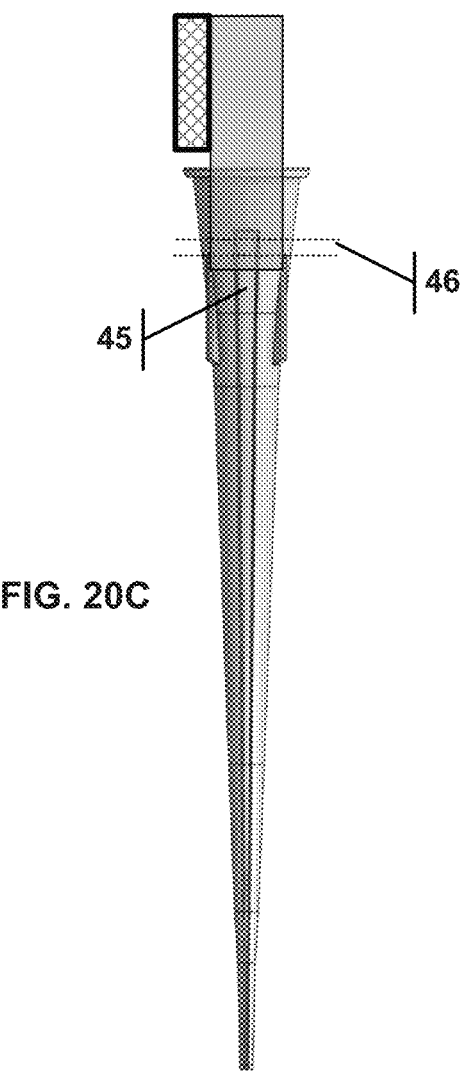
FIG. 20C illustrates another potential shortcoming of using existing pipetters that do not use an ejection bar positioned at the correct distance to form an optimal seal.

An existing pipetter 109 may have a distal edge 110 of the ejection bar 100 a distance of $D_{old}$ from the suction lumen opening 95, as shown in FIG. 20A. If $D_{old}$ is too short, as shown in FIG. 20B, then suction lumen 95 will not reach the low-force stretch region 46 of the pipette tip because the ejection bar will prevent further insertion; thus, the pipetter 109 will not seal with the pipette tip. If $D_{old}$ is too long, as shown in FIG. 20C, then suction lumen 95 will extend far into the pipette tip past the low-force stretch region 46 and may seal with the pipette tip, but will do so with a large insertion force. Also. the ejection bar has done nothing to regulate the insertion distance in this case. Ejecting the pipette tip in FIG. 20C will require a large, fatigue-inducing ejection force. FIG. 20C illustrates the current design of many pipette tip systems.

Figure 21:
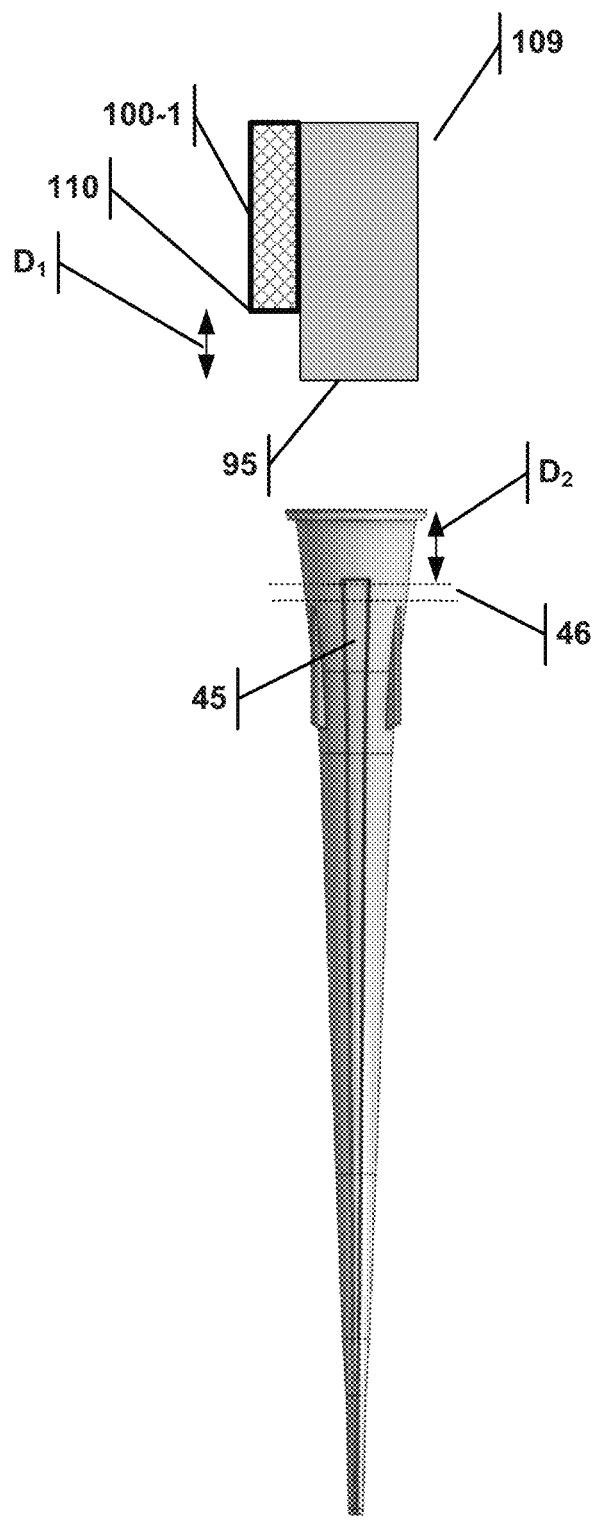
FIG. 21 illustrates a modified pipetter.
Figure 22:
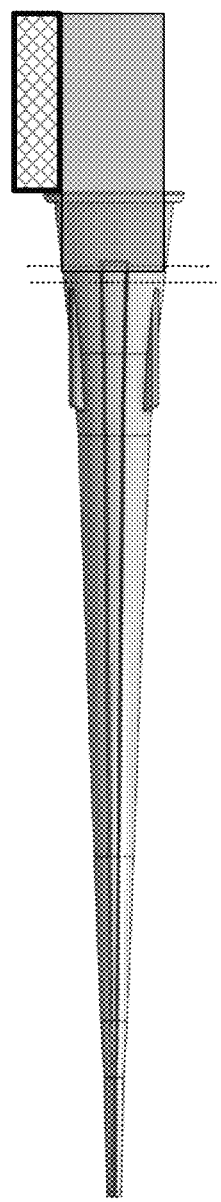
FIG. 22 illustrates the modified pipetter inserted into a pipette tip.

By replacing the ejection bar with one of an appropriate length, existing pipetters can be modified to effectuate the positive stop described above. Specifically, changing the ejection bar (shown as part 100-1 in FIG. 21) to have a distal edge 110 in an unengaged position that is a distance $D_1$ from the suction lumen opening 95 that is approximately the same distance as the distance $D_2$ between the rim 27 and the low-force stretch region 46 results in a positive stop system. This is shown graphically in FIGS. 21 and 22. This allows users to continue using existing equipment with slight modification, achieving a low-force positive stop system that is highly reliable and reduces user fatigue.

The invention has been described in connection with specific embodiments that illustrate examples of the invention but do not limit its scope. Various example systems have been shown and described having various aspects and elements. Unless indicated otherwise, any feature, aspect or element of any of these systems may be removed from, added to, combined with or modified by any other feature, aspect or element of any of the systems. As will be apparent to persons skilled in the art, modifications and adaptations to the above-described systems and methods can be made without departing from the spirit and scope of the invention, which is defined only by the following claims. Moreover, the applicant expressly does not intend that the following claims "and the embodiments in the specification to be strictly coextensive." *Phillips* v. *AHW Corp.*, 415 F.3d 1303, 1323 (Fed. Cir. 2005) (en banc).

The invention claimed is:

1. A pipette tip system for use with a plurality of pipette tips (10A, 10B, 10C), the system comprising:
   a base (70) with a floor (70-1);
   a support card (50A, 50B) that mates with the base (70) comprising:
      a support card top surface (56) comprising an array of pipette tip receiver openings (52) arranged in a N×M array, wherein the N is less than M and wherein each in the array comprises a receiver opening conical edge (55) extending from top surface (56), wherein the receiver opening conical edge (55) is steeper than the top surface, the receiver opening conical edge constructed to abut the pipette tip and provide the support to suspend the pipette tip above the base floor (70-1);
      a short-side card rail edge (66B) on an edge of the support card along the N side of the array, the short-side card rail edge (66B) flush with the support card top surface (56); and
      a long-side card rail edge (66A) on an edge of the support card along the M side of the array, the long-side card rail edge (66A) flush with the support card top surface (56);
   a support card lid (60) comprising:
      a long-side lid rail edge (65A) extending from a support card lid first surface (61), which is adapted to slidably mate with the long-side card rail edge (66A); and
      a short-side lid rail edge (65B) extending from a support card lid second surface (62), which is adapted to slidably mate with the short-side card rail edge (66B);
   a plurality of pipette tips (10A, 10B, 10C) disposed of in the array of pipette tip receiver openings (52).

2. The pipette tip system of claim 1, wherein when the long-side lid rail edge (65A) slidably mates with the long-side card rail edge (66A), the lid (60) can be positioned to expose fewer than all of the pipette receiver openings (52) in the array.

3. The pipette tip system of claim 1, wherein when the short-side lid rail edge (65B) slidably mates with the short-side card rail edge (66B), the lid (60) can be positioned to expose fewer than all of the pipette receive openings (52) in the array.

4. The pipette tip system of claim 1, wherein the support card (50A, 50B) and the base (70) comprise a tongue-and-groove mating system.

5. The pipette tip system of claim 1, wherein the base (70) comprises an interlocking structure (75A, 75B) constructed to mate with an adjacent base.

6. The pipette tip system of claim 5, further comprising a second support card and a second base, wherein the second base comprises a second interlocking structure, wherein the interlocking structure of the base and the second interlocking structure of the second base are mated.

7. The pipette tip system of claim 1, wherein the support card comprises an apron (51) extending away from the top surface (56).

8. The pipette tip system of claim 1, wherein the array pipette tip receiver openings (52) is adapted to receive the pipette tips (10A, 10B, 10C) of different sizes.

9. The pipette tip system of claim 1,
wherein each in the plurality of pipette tips (10A, 10B, 10C) has a distal end (15);
wherein the support card lid (60) is configured to prevent the distal ends (15) of the pipette tips (10A, 10B, 10C) from contacting one another when the support card lid (60) is mated to the support card (50A, 50B).

10. The pipette tip system of claim 1, wherein each in the array of pipette tip receiver openings (52) is constructed to receive and support a pipette tip (10A, 10B, 10C) with a rim (27) such that when the pipette tip (10A, 10B, 10C) is disposed in the pipette tip receiver opening (52), the rim (27) is flush with the support card top surface (56).

11. The pipette tip system of claim 1, wherein the receiver opening conical edge (55) comprises a transition conical edge (57) extending away from the top surface (56).

\* \* \* \* \*